United States Patent
Burnam

(10) Patent No.: US 12,171,901 B2
(45) Date of Patent: *Dec. 24, 2024

(54) POWDERED COLLAGEN WOUND CARE COMPOSITIONS

(71) Applicant: GLOBAL HEALTH SOLUTIONS, INC., Westlake Village, CA (US)

(72) Inventor: Bradley Burnam, Calabasas, CA (US)

(73) Assignee: GLOBAL HEALTH SOLUTIONS, INC., Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/087,128

(22) Filed: Dec. 22, 2022

(65) Prior Publication Data

US 2023/0128692 A1 Apr. 27, 2023

Related U.S. Application Data

(63) Continuation of application No. 17/589,629, filed on Jan. 31, 2022, now Pat. No. 11,565,020.

(60) Provisional application No. 63/253,525, filed on Oct. 7, 2021, provisional application No. 63/143,940, filed on Jan. 31, 2021.

(51) Int. Cl.
*A61L 26/00* (2006.01)

(52) U.S. Cl.
CPC ....... *A61L 26/0033* (2013.01); *A61L 26/0057* (2013.01); *A61L 2300/606* (2013.01); *A61L 2300/802* (2013.01)

(58) Field of Classification Search
None
See application file for complete search history.

(56) References Cited

U.S. PATENT DOCUMENTS

| | | |
|---|---|---|
| 2014/0234419 A1 | 8/2014 | McAnulty et al. |
| 2016/0367676 A1 | 12/2016 | Burnam |
| 2017/0354754 A1 | 12/2017 | Liden |
| 2019/0015548 A1 | 1/2019 | Harrell |
| 2020/0397869 A1 | 12/2020 | Leung et al. |
| 2020/0405637 A1 | 12/2020 | Burnam |

*Primary Examiner* — Robert A Wax
*Assistant Examiner* — Quanglong N Truong
(74) *Attorney, Agent, or Firm* — Womble Bond Dickinson (US) LLP

(57) ABSTRACT

Powdered collagen compositions and methods for wound care or the dressing or treatment of wounds in a subject in need thereof. The powdered collagen wound care composition includes powdered collagen or collagen-based material substantially covered with a hydrophobic barrier. In at least some instances, the hydrophobic barrier prevents the complete absorption or dissolution of the powdered collage or collagen-based material when placed on or in a wound or body of a subject for at least three (3) days. The powdered collagen wound care compositions are suitable for dressing or packing wounds or post-surgical incisions.

19 Claims, 2 Drawing Sheets

POWDERED COLLAGEN WOUND CARE COMPOSITIONS

CROSS-REFERENCE TO RELATED APPLICATIONS

This application is a continuation of U.S. application Ser. No. 17/589,629, filed Jan. 31, 2022, which claims the benefit of priority to U.S. Provisional Application Ser. No. 63,143,940, titled "Collagen Wound Care Compositions," filed Jan. 31, 2021, and U.S. Provisional Application Ser. No. 63/253,525, titled "Powdered Collagen Wound Care Compositions," filed Oct. 7, 2021, the entire contents of which are hereby incorporated by reference, for all purposes, in their entirety.

FIELD

The present disclosure is broadly concerned with collagen wound care compositions and methods for the treatment of wounds. The disclosure is also concerned with collagen compositions for the treatment of wounds that include powdered collagen or collagen-based material substantially covered with a hydrophobic barrier, as well as the use of such compositions as wound dressings or post-surgical dressings. The hydrophobic barrier may optionally include one or more preservatives.

BACKGROUND

Wound care in patients and animals is a common clinical challenge faced by the healthcare and veterinary industries. Wounds may include, for example, trauma wounds, burns, ulcers, lesions, abscesses, diabetic wounds, pressure sores or ulcers, and grafts or wounds resulting from surgical procedures and operations. Wounds may result from physical injury, surgical procedures and operations, heat or chemical burns, pressure on the skin, radiation, infections, immune system deficiencies, malnourishment, as well as various medical conditions such as vascular disorders and diabetes.

Collagen is known to improve wound healing and stimulate tissue growth and is well-tolerated at the wound site. In particular, collagen is thought to aid in the migration of fibroblasts and keratinocytes to the wound site thereby improving tissue growth in the wound bed. However, a potential problem with collagen and collagen-based wound care treatments is that collagen can completely dissolve or otherwise be absorbed by the body or wound site in less than three (3) days, resulting in inadequate treatment and/or protection of the wound site as well as overly frequent reapplication or retreatment. The dissolution and absorption of collagen and collagen-based materials at the wound site is facilitated by the fact that collagen tends to absorb blood and other bodily fluids. As a result, the dissolution and absorption at the wound site of collagen or collagen-based materials is especially problematic for powdered collagen or powdered collagen-based materials due to their small particle size and increased surface area for the absorption of fluids. Accordingly, improved collagen wound care compositions are desirable.

BRIEF DESCRIPTION OF THE DRAWINGS

In order to describe the manner in which the advantages and features of the disclosure can be obtained, reference is made to embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
FIG. 1 is a photograph of the presently disclosed collagen wound care composition showing its characteristic fluffy or unconsolidated texture suitable for wound packing, according to an exemplary embodiment of the present disclosure.

According to a first aspect of the present disclosure, a powdered collagen wound care composition is provided. The powdered collagen wound care composition may include powdered collagen or collagen-based material that is substantially covered with a hydrophobic barrier. The hydrophobic barrier gives structure to the powdered collagen or collagen-based material so that the powdered collagen wound care composition may be effectively applied to a wound site thereby protecting the wound site with a sterile covering and providing a barrier to the loss of blood and other bodily fluids. Additionally, the hydrophobic barrier provides a barrier around the powdered collagen that slows or prevents blood and other bodily fluids from absorbing or permeating into the powdered collagen thereby causing the powdered collagen to dissolve or otherwise be absorbed by the body.

According to at least one aspect, the presently disclosed collagen wound care composition comprises powdered collagen or a powdered collagen-based material and a hydrophobic barrier. The hydrophobic barrier at least partially coats the surface of the powdered collagen or powdered collagen-based material. The hydrophobic barrier may be in the form of a coating that at least partially surrounds or is otherwise adsorbed to the surface of the powdered collagen or powdered collagen-based material.

The hydrophobic coating is effective to reduce the dissolution rate or the rate of absorption of the powdered collagen or collagen-based material by the wound or body when placed in or on a wound in a subject in need thereof. In at least some instances, the hydrophobic barrier surrounding the powdered collagen or collagen-based material prevents the complete absorption and/or dissolution of the powdered collage or collagen-based material for at least three (3) days when placed on or in a wound or body of a subject. This may also be true even when the wound site and/or one or more tissues surrounding the wound is characterized as having a good blood supply. In some instances, the hydrophobic barrier prevents the complete absorption and/or dissolution of the powdered collagen or collagen-based material for at least seven (7) days when placed on or in a wound or body of a subject.

In some instances, the hydrophobic barrier may optionally include one or more preservatives. In such instances, the hydrophobic barrier may be an oil-based antimicrobial composition as described throughout the present disclosure. In some instances, the hydrophobic barrier may include from about 0.001% by weight to about 5% by weight of the one or more preservatives. When the hydrophobic barrier includes one or more preservatives, the preservative in the hydrophobic barrier helps to maintain the sterility of the wound site as well as the sterility of the wound care composition itself. Accordingly, the preservative in the hydrophobic barrier facilitates sterile packing of the wound site by the powdered collagen wound care composition as well as maintenance of a sterile wound site environment, thereby effectively preventing or treating infection at the wound site.

The one or more preservatives included in the hydrophobic barrier may be selected from the group consisting of polyhexamethylene biguanide (PHMB), polyaminopropyl biguanide (PAPB), benzalkonium chloride, cetrimide, chlorhexidine, polihexanide biguanide, polihexanide, polyhexamethylene guanide, poly(iminoimidocarbonyl-iminoimidocarbonyl-iminohexamethylene), and any salt or combination thereof. In some instances, the one or more preservatives comprises polyhexamethylene biguanide (PHMB). In such instances, the hydrophobic barrier may comprise from about 0.05% to about 5% by weight PHMB. The one or more preservatives may comprise a cationic biocide. The one or more preservatives may also be selected from the group consisting of benzalkonium chloride, cetrimide, chlorhexidine, and any salt or combination thereof. In some cases, the hydrophobic barrier may include from about 0.001% to about 0.15% by weight benzalkonium chloride (BZK). In other instances, the hydrophobic barrier comprises from about 0.05% to about 5% by weight polyaminopropyl biguanide (PAPB).

In at least some instances, the hydrophobic barrier may include a polar solvent in which the one or more preservatives are dissolved. In such instances, the polar solvent containing the one or more preservatives is suspended in the hydrophobic barrier. In at least some instances, the polar solvent and the one or more preservatives are suspended as microdroplets or nanodroplets in the hydrophobic barrier. According to at least one aspect, the polar solvent comprising one or more preservatives does not separate from the hydrophobic barrier for at least 6 months. The polar solvent may be selected from the group consisting of water, ethanol, a mixture of water and ethanol, acetic acid, and any combination thereof. In at least some instances, the solvent containing the one or more preservatives may be suspended in the hydrophobic without the use of an added emulsifier.

In at least some instances, the hydrophobic barrier is at least partially adsorbed to the surface of the powdered collagen or collagen-based material. In some cases, the hydrophobic barrier at least partially coats the surface of the powdered collagen or collagen-based material. In other instances, the hydrophobic barrier substantially coats the powdered collagen or collagen-based material. In still other instances, the hydrophobic barrier may form a coat on the powdered collagen or collagen-based material. In such instances, the powdered collagen or collagen-based material is coated with the hydrophobic barrier.

The powdered collagen or collagen-based material may comprise a plurality of particles comprising collagen or collagen-based material. The plurality of particles may be at least partially coated with the hydrophobic barrier. In some instances, the plurality of particles may be substantially coated with the hydrophobic barrier. In other instances, the hydrophobic barrier is at least partially adsorbed to the surface of the plurality of particles. As used herein, the terms "adsorbed" and "adsorption," in all their forms refer to the adhesion of a composition, or molecules thereof, to a surface.

The hydrophobic barrier may comprise one or more oils. In at least some instances, the hydrophobic barrier may comprise greater than about 80% by weight oil. The one or more oils may be selected from the group consisting of animal oil, vegetable oil, natural oil, synthetic oil, hydrocarbon oils, silicone oils, and semi-synthetic derivatives thereof, and any combination thereof. The one or more oils may be coconut oil in some instances.

In at least some instances, the one or more oils is selected from the group consisting of mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, C12-15 alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*Simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combination thereof.

In other instances, the one or more oils may be petrolatum. In some instances, the one or more oils comprises greater than about 80% by weight petrolatum. In some cases, the hydrophobic barrier comprises greater than about 80% by weight petrolatum.

The powdered collagen wound care composition may comprises from about 45 weight percent to about 85 weight percent powdered collagen or collagen-based material, or from about 50 weight percent to about 80 weight percent powdered collagen or collagen-based material, or from about 60 weight percent to about 80 weight percent powdered collagen or collagen-based material, or from about 65 weight percent to about 85 weight percent powdered collagen or collagen-based material, or from about 75 weight percent to about 85 weight percent powdered collagen or collagen-based material. The powdered collagen wound care composition may also comprise from about 15 weight percent to about 55 weight percent hydrophobic barrier, or from about 20 weight percent to about 50 weight percent hydrophobic barrier, or from about 20 weight percent to about 40 weight percent hydrophobic barrier, or from about 15 weight percent to about 35 weight percent hydrophobic barrier, or from about 15 weight percent to about 25 weight percent hydrophobic barrier.

The powdered collagen wound care composition may, at least in some instances, have a fluffy or unconsolidated texture especially suited for wound packing and care, as shown in FIG. 1. In at least some instances, the hydrophobic barrier does not separate from the collagen or collagen-based material for at least 6 months.

In at least some instances, the powdered collagen or collagen-based material is characterized by an average particle size of from about 5 microns to about 80 microns. In some cases, the powdered collagen or collagen-based material is micronized collagen. The powdered collagen or collagen-based material may be characterized by an average particle size of from about 5 microns to about 80 microns, or from about 20 microns to about 70 microns, or from about 5 microns to about 30 microns, or from about 10 microns to about 30 microns, or from about 15 microns to about 30 microns. In some instances, the powdered collagen or collagen-based material is characterized by an average particle size of less than 20 microns or less than 30 microns.

In at least some instances, the powdered collagen or collagen-based material is sourced or obtained from bovine collagen, such as Type-1 bovine collagen. The collagen or collagen-base material may be a material selected from extracellular matrix materials, micronized extracellular matrix, purified collagen, Type I collagen, Type II collagen, Type III collagen, Type X collagen, collagen fibers, collagen fibrils, micronized collagen, defibrillated collagen, coarse collagen bundles, non-crosslinked collagen, non-mineralized collage, collagen treated to control cross-linking (e.g., via chemical, thermal, photo, or radiation-induced cross-linking), collagen-glycosaminoglycan (GAG) mixtures, and any combination thereof.

The powdered collagen wound care composition may be prepared by mixing the powdered collagen or collagen-based material with the hydrophobic barrier without heating. In some cases, the collagen wound care composition is prepared by mixing the powdered collagen or collagen-based material with the hydrophobic barrier at a temperature from about 0 degrees Celsius to about 25 degrees Celsius. The hydrophobic barrier may be prepared by a process comprising: a) dissolving the one or more preservatives in a polar solvent to give a preservative solution; b) heating an oil to a temperature sufficient to cause the oil to melt or to a temperature sufficient to provide a oil having a density capable of suspending the polar solvent comprising one or more preservatives, resulting in a melted oil; c) heating the preservative solution to a temperature higher than the temperature of the melted oil to give a heated preservative solution; d) mixing the melted oil and the heated preservative solution to give a melted mixture; and e) cooling the melted mixture to give the hydrophobic barrier. In some instances, the heated preservative solution has a temperature that is about 1° C. to about 5° C. higher than the temperature of the melted oil at the time of mixing.

According to a second aspect of the present disclosure, a method of treating or dressing a wound or a post-surgical incision in a subject is provided. The method includes applying the powdered collagen wound care composition according to the first aspect of the present disclosure to a wound or post-surgical incision in need of dressing or treatment. The method may further include contacting the powdered wound care composition to a wound covering, wherein the wound covering is a selected from the group consisting of a bandage, wrap, gauze, sponge, and film; and applying the wound covering to the wound or post-surgical skin graft in need of treatment. The method may further include packing the wound or post-surgical incision with the powdered collagen wound care composition according to the first aspect of the present disclosure. The method may further include applying a wound covering to the packed wound or post-surgical incision. In at least some instances, the powdered collagen wound care composition may be pre-wetted or hydrated by contacting the composition with a sterile saline solution or aqueous solution to form a paste which may then be used to pack the wound. Hydrating the composition to form a paste may be especially useful when the wound does not have sufficient blood supply as a result of vascular insufficiency.

According to a third aspect of the present disclosure, a system for treating or dressing a wound or a post-surgical incision in a subject is provided. The system may include a powdered collagen wound care composition according to the first aspect of the present disclosure and a wound covering. The wound covering in the system is operable to cover the wound once it is treated or packed with the collagen wound care composition.

Figure 2:
FIG. 2 is a photograph of the collagen wound care composition in sterile packaging suitable for commercial transport and application to a wound site in a subject in need thereof.

According to a fourth aspect of the present disclosure, a kit for treating or dressing a wound or a post-surgical incision in a subject is provided. The kit may include a packaging containing a powdered collagen wound care composition according to the first aspect of the present disclosure, for example, as shown in FIG. 2. The packaging may be selected from the group consisting of a screw-cap cylindrical tube or vial, a snap-cap cylindrical tube or vial, a screw-cap or snap-cap collapsible tube or squeeze tube, and any combination thereof.

According to a fifth aspect of the present disclosure, a collagen wound care composition for the treatment or dressing of a wound is provided. The collagen wound care composition may include from about 45 weight percent to about 85 weight percent collagen or collagen-based material. The collagen wound care composition may also include from about 15 weight percent to about 55 weight percent oil-based antimicrobial composition. The oil-based antimicrobial composition may be fused to, or at least partially adsorbed, to the collagen-based material.

The presently disclosed collagen wound care compositions exhibit unexpected absorbency and antimicrobial effectiveness, thereby providing a self-sterilizing regenerative wound matrix that is malleable and capable of stimulating healing while reducing bioburden and absorbing drainage. The collagen wound care composition comprises an oil-based antimicrobial composition fused to or otherwise adsorbed to powdered collagen or collagen-based material.

It has been unexpectedly discovered that the presently disclosed collagen wound care compositions comprising micronized or powdered collagen fused to a oil-based antimicrobial composition comprising one or more polar antimicrobial ingredients, such as polyhexamethylene biguanide (PHMB), suspended in an oil-based carrier, are especially effective in the treatment of wounds. In particular, it has been discovered that the presently disclosed compositions provide for improved penetration and absorption of collagen throughout the wound site, thereby enabling efficient delivery of collagen to the wound bed. It has also been unexpectedly been found that presently disclosed PHMB and collagen compositions, when prepared according to the presently disclosed techniques, synergistically results in improved wound healing and lower incidence of infection as compared to separate administration of oil-based antimicrobial compositions and collagen compositions. In some instances, the oil-based antimicrobial composition melts or otherwise liquefies once applied to the wound site due to the heat of the skin and wound, causing the release or increasing the availability of the antimicrobial composition and collagen to the wound site and aiding in the absorption and penetration of the collagen and antimicrobial ingredients by the wound site.

The collagen wound care composition may comprises from about 50 weight percent to about 80 weight percent collagen or collagen-based material, or from about 60 weight percent to about 80 weight percent collagen or collagen-based material, or from about 65 weight percent to about 85 weight percent collagen or collagen-based material, or from about 75 weight percent to about 85 weight percent collagen or collagen-based material. The collagen wound care composition may also comprise from about 20 weight percent to about 50 weight percent oil-based antimicrobial composition, or from about 20 weight percent to about 40 weight percent oil-based antimicrobial composition, or from about 15 weight percent to about 35 weight percent oil-based antimicrobial composition, or from about 15 weight percent to about 25 weight percent oil-based antimicrobial composition.

The oil-based antimicrobial composition may include an oil-based carrier and a polar solvent comprising one or more polar antimicrobial agents. The polar solvent may include one or more polar antimicrobial agents suspended in the oil-based carrier. In at least some instances, the oil-based antimicrobial composition does not separate from the collagen or collagen-based material for at least 6 months and the polar solvent comprising one or more antimicrobial agents does not separate from the oil-based carrier for at least 6 months.

The collagen or collagen-based material may be in powdered or micronized form. In at least some instances, the collagen or collagen-based material is characterized by an average particle size of from about 5 microns to about 80 microns. The collagen or collagen-based material may be capable of absorbing at least 20 times its weight. The collagen or collagen-based material may be prepared with a pH under 4 or comprise a pH under 4. It has been discovered that collagen or collagen-based material prepared under low pH conditions has elevated antimicrobial properties. In at least some instances, the collagen or collagen-based material is sourced or obtained from bovine collagen, such as Type-1 bovine collagen.

The oil-based antimicrobial composition included in the collagen wound composition may include an oil-based carrier and a polar solvent comprising one or more polar antimicrobial agents. The polar solvent comprising one or more polar antimicrobial agents is suspended in the oil-based carrier. In at least some instances, the polar solvent comprising the one or more antimicrobial agents is dispersed in the oil-based carrier to form a stable suspension such that the solvent and polar antimicrobial agent does not separate from the oil-based carrier for at least six months.

In at least some instances, the collagen or collagen-based material is in powdered form. In some cases, the collagen or collagen-based material is micronized collagen. The collagen or collagen-based material may be characterized by an average particle size of from about 5 microns to about 80 microns, or from about 20 microns to about 70 microns, or from about 5 microns to about 30 microns, or from about 10 microns to about 30 microns, or from about 15 microns to about 30 microns. In some instances, the collagen or collagen-based material is characterized by an average particle size of less than 20 microns or less than 30 microns.

The collagen or collagen-base material may be a material selected from extracellular matrix materials, micronized extracellular matrix, purified collagen, Type I collagen, Type II collagen, Type III collagen, Type X collagen, collagen fibers, collagen fibrils, micronized collagen, defibrillated collagen, coarse collagen bundles, non-crosslinked collagen, non-mineralized collage, collagen treated to control cross-linking (e.g., via chemical, thermal, photo, or radiation-induced cross-linking), collagen-glycosaminoglycan (GAG) mixtures, and any combination thereof.

The oil-based based carrier may be selected from animal oil, vegetable oil, natural oil, synthetic oil, hydrocarbon oils, silicone oils, and semi-synthetic derivatives thereof, and any combination thereof. The oil-based carrier may also be petrolatum, cocoa butter, jojoba oil, olive oil, soybean oil, coconut oil, beeswax, lanolin wax, carnauba wax, stearic acid, or any mixture thereof. The oil-based carrier may also be mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, C12-15 alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*Simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combination thereof.

In some instances, the polar solvent may be water, ethanol, or a mixture of ethanol and water. In some cases, the polar solvent may further include acetic acid. In some aspects, the one or more polar antimicrobial agents comprises a cationic biocide. The cationic biocide may be benzalkonium chloride, cetrimide, chlorhexidine, polihexanide biguanide (polihexanide, polyhexamethylene biguanide, polyhexamethylene guanide, poly(iminoimidocarbonyl-iminoimidocarbonyl-iminohexamethylene), poly (hexamethylenebiguanide), polyaminopropyl biguanide), and salts or combinations thereof. The polar solvent may further include a preservative selected from the group consisting of benzalkonium chloride, cetrimide, chlorhexidine, and any combination thereof. In some instances, the oil-based antimicrobial composition comprises from about 0.001% to about 0.15% by weight benzalkonium chloride (BZK). In other instances, the oil-based antimicrobial composition comprises from about 0.001% to about 0.01% by weight or from about 0.005% to about 0.007% by weight benzalkonium chloride (BZK).

The oil-based antimicrobial compositions may further include one or more therapeutic agents selected from the group consisting of stem cells, TGF-alpha, TGF-beta (TGFβ1, TGFβ2, TGFβ3), platelet-derived growth factor (PDGF), epidermal growth factor (EGF), fibroblast growth factor also referred to as keratinocyte growth factor (FGF1, FGF2, FGF4, FGF7), vascular endothelial growth factor (VEGF), insulin-like growth factor (IGF), connective tissue growth factor (CTGF), activin, interleukin-1 (IL1α, IL1β), TNFα, GM-CSF, a powdered antibiotic, an antifungal agent, a hemostatic agent, cytokines, and hyaluronic acid.

The presently disclosed collagen wound care composition may be prepared by mixing the collagen or collagen-based material with the oil-based antimicrobial composition without heating. In some instances, the collagen wound care composition may be prepared by mixing the collagen or collagen-based material with the oil-based antimicrobial composition at a temperature from about 0 degrees Celsius to about 25 degrees Celsius.

According to at least one aspect of the present disclosure, the oil-based antimicrobial compositions may be prepared by a process that includes: a) dissolving the one or more polar antimicrobial agents in a polar solvent to give an antimicrobial agent solution; b) heating the oil-based carrier to a temperature sufficient to cause the oil-based carrier to melt or to a temperature sufficient to provide a oil-based carrier density capable of suspending the polar solvent comprising one or more polar antimicrobial agents, resulting in a melted oil-based carrier; c) heating the antimicrobial agent solution to a temperature higher than the temperature of the melted oil-based carrier to give a heated antimicrobial solution; d) mixing the melted oil-based carrier composition and the heated antimicrobial solution to give a melted mixture; and e) cooling the melted mixture to give the oil-based antimicrobial composition. In some instances, the heated antimicrobial solution has a temperature that is about 1° C. to about 5° C. higher, or about 1° C. to about 10° C. higher, or about 1° C. to about 15° C. higher, than the temperature of the melted oil-based carrier at the time of mixing.

In some instances, the polar antimicrobial agent is polyhexamethylene biguanide (PHMB) and the oil-based carrier is petrolatum. In such instances, the PHMB may be dissolved in a polar solvent to form a PHMB solution and the PHMB solution dispersed in the petrolatum containing collagen. According to at least one aspect, the petrolatum-based PHMB compositions contain no emulsifier.

The presently disclosed petrolatum-based PHMB compositions may be prepared by a process that includes: a) dissolving the PHMB in a polar solvent to give a PHMB solution; b) heating the petrolatum to a temperature sufficient to cause the petrolatum to melt to give a melted petrolatum; c) heating the PHMB solution to a temperature higher than the temperature of the melted petrolatum to give a heated PHMB solution; d) mixing the melted petrolatum and the heated PHMB solution to give a melted mixture; and e) cooling the melted mixture to give the petrolatum-based PHMB composition. In some instances, the PHMB solution is heated to a temperature that is about 1° C. to about 5° C. higher than the temperature of the melted petrolatum. According to at least one aspect of the present disclosure, the resultant petrolatum-based PHMB composition does not require an emulsifier to form a stable suspension of PHMB dispersed in the petrolatum. Further, the petrolatum-based PHMB composition prepared according to this process does not require high shear mixing to form a stable suspension of PHMB in petrolatum in the absence of an added emulsifier.

In instances in which the oil-based carrier is petrolatum, the oil-based antimicrobial composition may include greater than about 60% by weight petrolatum, or greater than about 70% by weight petrolatum, or greater than about 80% by weight petrolatum, or greater than about 90% by weight petrolatum. According to one aspect, the presently disclosed oil-based antimicrobial compositions may include from about 0.1% to about 1% by weight PHMB, or from about 0.05% to about 5% by weight PHMB, or from about 0.05% to about 3% by weight PHMB, or from about 0.2% to about 0.6% by weight PHMB, or from about 0.3% to about 0.5% by weight PHMB, or from about 0.1% to about 3.5% by weight PHMB, or from about 0.05% to about 2.5% by weight PHMB, or from about 0.5% to about 3% by weight PHMB, or from about 0.5% to about 2.5% by weight PHMB, or from about 1.5% to about 2.5% by weight PHMB.

PHMB is closely related to the polymeric biguanide polyaminopropyl biguanide (PAPB). Therefore, in at least some instances, polyaminopropyl biguanide (PAPB) may be substituted for the PHMB in the presently disclosed oil-based antimicrobial compositions and methods. For example, the oil-based antimicrobial compositions may include from about 0.005% to about 5% by weight PAPB, or from about 0.01% to about 5% by weight PAPB, or from about 0.05% to about 5% by weight PAPB, or from about 0.05% to about 3% by weight PAPB, or from about 0.1% to about 1% by weight PAPB, or from about 0.2% to about 0.6% by weight PAPB, or from about 0.3% to about 0.5% by weight PAPB, or from about 0.1% to about 3.5% by weight PAPB, or from about 0.05% to about 2.5% by weight PAPB, or from about 0.5% to about 3% by weight PAPB, or from about 0.5% to about 2.5% by weight PAPB, or from about 1.5% to about 2.5% by weight PAPB.

According to a sixth aspect of the present disclosure, a method of treating or dressing a wound in a subject is provided. The method includes applying the presently disclosed compositions to a wound, post-surgical wound, or a post-surgical incision in need of dressing or treatment. The method may further include covering the composition with a wound covering selected from the group consisting of a bandage, wrap, gauze, sponge, and film, following the application of the composition to the wound or incision in need of treatment. According to one aspect of the present disclosure, the method of treating or dressing a wound in a subject may include contacting the presently disclosed compositions to a wound covering, wherein the wound covering is a selected from the group consisting of a bandage, wrap, gauze, sponge, skin graft, and film. The method may further include applying the wound covering to the wound, incision, or graft in need of treatment.

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1. Hydrophobic Barrier with Preservative/Oil-Based Antimicrobial Composition (Formulation Example 1)

Formulation Example 1 was prepared by adding 2540.3 pounds of white petrolatum to a tank that has been cleaned and sterilized in accordance with SOP protocol. In the tank was used to heat the petrolatum to 110° C.-113° F. to melt the petrolatum. In a separate clean and sanitized container 133.70 pounds of water and the desired amount of BZK and PHMB were added and heated to 122° F. When both phases are at temperature, the solution phase was slowly added to the petrolatum with mixing. The heat was decreased slowly to 96-104° F. The product was tested for quality control and transferred to polypropylene drums. The resulting composition was shiny and white to slightly yellow in appearance. Specific gravity at 25° C. matches specification when it is from 0.830-0.910. Viscosity at @25° C. TF@10 rpm matches specification when it is from about 225,000-300,000 cps. The final formulation contained the following ingredients by weight percent: 95% petrolatum; 0.13% BZK, 0.2% PHMB, and 4.67% water.

Example 2. Skin Sensitization Evaluation

A study was conducted on the formulation prepared in Example 1, referred to herein as "Formulation Example 1" to assess skin sensitization. Patches comprising Formulation 1 were affixed directly to the skin of 53 human study participants representing an age range from 18-63 and five skin types. Table 1 presents the participant demographics. Patches remained in place for 48 hours after the first application. Participants were instructed not to remove the patches prior to their 48 hour scheduled visit. Thereafter, the subjects were instructed to remove patches for 24 hours. This procedure was repeated until a series of nine consecutive, 24 hour exposures had been made three times per week for three consecutive weeks. Test sites were evaluated by trained personnel. Following a 10-14 day rest period, a retest/challenge dose was applied once to a previously unexposed test site. Test sites were evaluated by trained personnel 48 and 96 hours after application. The sites were scored based on the International Contact Dermatitis Research Group scoring scale (Rietschel, Fowler, Ed., Fisher's Contact Dermatitis (fourth ed.). Baltimore, Williams & Wilkins, 1995) as presented in Table 2.

TABLE 1

| Participant Demographics. | |
|---|---|
| Number of subjects enrolled | 53 |
| Number of subjects completing study | 53 |

TABLE 1-continued

| Participant Demographics. | |
|---|---|
| Age Range | 18-63 |
| Sex | Male 13 |
| | Female 40 |
| Fitzpatrick Skin Type* | |
| 1-always burn, does not tan | 0 |
| 2-burn easily, tan slightly | 4 |
| 3-burn moderately, tan progressively | 47 |
| 4-burn a little, always tan | 2 |
| 5-rarely burn, tan intensely | 0 |
| 6-never burn, tan very intensely | 0 |

*Agaghe P, Hubert P. Measuring the skin. (p. 473, table 48.1) Springer-Verlag Berlin Heidelberg, 2004.

TABLE 2

| Scoring Scale. | |
|---|---|
| 0 | No reaction (negative) |
| 1 | Erythema throughout at least ¾ of patch area |
| 2 | Erythema and induration throughout at least ¾ of patch area |
| 3 | Erythema, induration and vesicles |
| 4 | Erythema, induration and bullae |
| D | Site discontinued |
| Dc | Subject discontinued |

No adverse reactions of any kind were reported during the course of study. Accordingly, Formulation Example 1 gives no identifiable signs or symptoms of primary irritation or sensitization (contact allergy).

Example 3. Antimicrobial Efficiency Testing

Antimicrobial efficacy testing was conducted according to USP 51. Five microbes were tested. Each organism was inoculated at an inoculum level of $1 \times 10^6$ colony forming units (CFU) per gram for bacteria or $1 \times 10^5$ CFU per gram for yeast and mold. The inoculated samples were then stored at 20-25° C. for 28 days. The population of each microorganism was determined by plate counting at Day 2, 7, 14, 21, and 28. The plate counts were performed at a 1:10 initial dilution using Modified Letheen Broth as the diluent and plated onto Tryptic Soy and Sabouraud Dextrose agar.

A single application of Formulation Example 1 gave 100% elimination from day 2 to day 28 for all microbes tested (Table 3). Given the 100% elimination, there was a 4 log reduction in the yeast/mold species and a 5 log reduction in the bacterial species (Table 4). Table 5 is a positive control indicating that the method used recovers 80-100% of the microbe in the absence of Formulation Example 1. Accordingly, the microbes present in the test sample were eliminated under the tested conditions. The results illustrate the broad spectrum of activity for Formulation Example 1.

TABLE 3

Preservative Testing.

| Organism | Inoculum/g | Colony Forming Units/gram | | | | |
|---|---|---|---|---|---|---|
| | | Day 2 | Day 7 | Day 14 | Day 21 | Day 28 |
| *Staphylococcus aureus* (bacteria) (ATCC #6538) | $1 \times 10^6$ | <10 | <10 | <10 | <10 | <10 |
| *Pseudomonas aeruginosa* (bacteria) (ATCC #9027) | $1 \times 10^6$ | <10 | <10 | <10 | <10 | <10 |
| *Escherichia coli* (bacteria) (ATCC #8739) | $1 \times 10^6$ | <10 | <10 | <10 | <10 | <10 |
| *Candida albicans* (yeast) (ATCC #10231) | $1 \times 10^5$ | <10 | <10 | <10 | <10 | <10 |
| *Aspergillus niger* (mold) (ATCC #16404) | $1 \times 10^5$ | <10 | <10 | <10 | <10 | <10 |

TABLE 4

Log Reduction Calculation from Initial Inoculum.

| | 14 days | 28 days |
|---|---|---|
| *Aspergillus niger* | 4.00 | 4.00 |
| *Candida albicans* | 4.00 | 4.00 |
| *Pseudomonas aeruginosa* | 5.00 | 5.00 |
| *Escherichia coli* | 5.00 | 5.00 |
| *Staphylococcus aureus* | 5.00 | 5.00 |

TABLE 5

Preservative Testing Validation.

| Organism | Inoculum | Dilution | Microbial Recovery | Diluent | Percent Recovery |
|---|---|---|---|---|---|
| *Staphylococcus aureus* | 76 cfu/plate | 1:10 | 69 cfu/plate | LB | 87% |
| *Pseudomonas aeruginosa* | 83 cfu/plate | 1:10 | 81 cfu/plate | LB | 97% |
| *Escherichia coli* | 68 cfu/plate | 1:10 | 58 cfu/plate | LB | 85% |
| *Candida albicans* | 63 cfu/plate | 1:10 | 50 cfu/plate | LB | 79% |
| *Aspergillus niger* | 60 cfu/plate | 1:10 | 60 cfu/plate | LB | 100% |

CFU = colony forming units; LB = Letheen Broth; Diluent = Letheen Broth; Dilution: 1:10

Example 4: Cytotoxicity Evaluation

The study was conducted to assess the biological reactivity of mammalian cells (grown in culture) to the agar-diffusible elements of Formulation Example 1.

The samples to be evaluated for cytotoxicity include test product comprising Formulation Example 1, Amber latex tubing as a positive control, and HDPE sheet stock as a negative control. The samples were sized to have no less than 100 mm² of contact surface and provide coverage of approximately 10% of the test dish. The dimensions of the test product comprising Formulation Example 1 were 1.1× 1.1-1.2 cm; the dimensions of the positive control were 1.0×2.55-2.7 cm; and the dimensions of the negative control were 1.15×1.0-1.2 cm. The manipulation of the samples was performed aseptically.

Prior to exposure to the samples, the L929 Mouse Fibroblast cells were subcultured in Minimum Essential Medium (MEM) with 10% Fetal Bovine Serum (FBS) to achieve a confluency of approximately 80±10% at the time of exposure. The cells were examined for normal morphology and the absence of contamination. Once the cells met the acceptance criteria for use, individual dishes were numbered in triplicate to represent the controls and the test product comprising Formulation Example 1.

On the day of testing, the subculture media was carefully removed from each test dish and replaced with a 2 mL aliquot of the 1:1 overlay medium (in equal parts of 2× Minimum Essential Medium (with 2% Fetal Bovine Serum) and Agar Noble). After allowing the overlay medium to solidify, a single test product comprising Formulation 1 or control sample was placed in the center of each dish (in contact with the agar surface). Triplicate cultures were prepared for each test product comprising Formulation 1 and positive and negative controls (one sample per dish). When the test product comprising Formulation 1 or positive/negative control has only one face designated for patient-contact, that "side" of the sample was directed toward the agar. The test dishes, along with 3 dishes with overlay medium only (Monolayer Negative Controls), were then placed in the 37° C./5% $CO_2$ incubator to initiate the exposure interval.

The dishes were incubated for 24 hours and then microscopically examined for an indication of cellular response. A preliminary microscopic examination of the cells was made prior to staining and before the control and test product comprising Formulation 1 were removed from the agar layer. The cells were then stained with a fresh working Neutral Red Solution to facilitate response grading. The test product comprising Formulation Example 1 and control samples were removed from the dishes at this time. The stained cells were then fixed by the addition of buffered formalin. Following fixation, the agar overall was removed from each dish. Following staining, the cellular responses were then evaluated microscopically and macroscopically (by examining the dishes against a white surface) and the results were recorded.

For the control samples to be deemed valid, the negative controls may be no greater than Grade 0 and the positive control may be no less than Grade 3. For the test product comprising Formulation 1, a Grade of 0, 1 (slight) or 2 (mild) indicates the test product comprising Formulation Example 1 "meets" the assay acceptance criteria and a Grade of 3 (moderate) or 4 (severe) indicates the test product comprising Formulation Example 1 does not meet the assay acceptance criteria. Table 6 depicts the Grading guidelines.

TABLE 6

Grading Guidelines.

| Grade(1) | Reactivity | Description of the Reactivity Zone(2) |
|---|---|---|
| 0 | None | No detectable zone around or under specimen |
| 1 | Slight | Some malformed or degenerated cells under specimen(3) |
| 2 | Mild | Zone limited to area under specimen |
| 3 | Moderate | Zone extends 0.45 to 1.0 cm beyond specimen |
| 4 | Severe | Zone extends greater than 1.0 cm beyond specimen |

(1): The use of the above Grading Table is contingent on the test article meeting the minimum surface area requirements of ≥100 mm². Should samples of smaller dimensions be tested, the reactivity (if any) would be expected to be less and the grading would need to be justified.
(2): The extent of the Reactivity Zone is the maximum measured distance from the edge of the specimen to the margin of monolayer where degenerated cells are no longer observed. Where described as "under specimen", this maximum measured distance is limited to <0.45 cm beyond the specimen.
(3): To be interpreted as "slight" reactivity, no more than 50% of the cells under the specimen may exhibit reactivity as rounding and/or lysis.

Table 7 depicts the results of the study. The assay controls met the acceptance criteria for a valid assay. All negative controls responses were no greater than Grade 0 and the positive control response were not less than Grade 3. The responses observed for the test product comprising Formulation Example 1 were interpreted according to the current USP guidelines. The Grade 1 response from the test product comprising Formulation Example 1 is considered to be "non-cytotoxic" (i.e. meets ISO test acceptance requirements of no more than Grade 2 reactivity). Accordingly, Formulation Example 1 does not damage mammalian cells.

TABLE 7

Study Results.

| | Macroscopic Reading (Zone Dimensions) | Microscopic Reading (% Rounded/ Lysed) | Grade |
|---|---|---|---|
| Monolayer Negative Control | 1 No detectable zone | 0%/0% | 0 |
| | 2 No detectable zone | 0%/0% | 0 |
| | 3 No detectable zone | 0%/0% | 0 |
| Material Positive Control | 1 Clear Zone 3.2 × 3.2; Greatest distance from specimen 1.5 cm | 100%/100 % | 4 |
| | 2 Clear Zone 3.2 × 3.2; Greatest distance from specimen 1.5 cm | 100%/100 % | 4 |
| | 3 Clear Zone 3.2 × 3.2; Greatest distance from specimen 1.5 cm | 100%/100 % | 4 |
| Material Negative Control | 1 No detectable zone | 0%/0% | 0 |
| | 2 No detectable zone | 0%/0% | 0 |
| | 3 No detectable zone | 0%/0% | 0 |
| Test Product Comprising Formulation 1 | 1 Entire dish lightly stained ~5% rounded directly under sample | 1.5%/1.5% | 1 |
| | 2 Entire dish lightly stained ~5% rounded directly under sample | 1.5%/1.5% | 1 |
| | 3 Entire dish lightly stained ~5% rounded directly under sample | 1.5%/1.5% | 1 |

Example 5: Rabbit Skin Irritation

The study was conducted to assess the irritating potential of Formulation Example 1 to produce dermal irritation.

Within 24 hours to 4 hours before test application, the backs of female albino New Zealand White rabbits were clipped free of hair, exposing 2 test and 2 control areas on each side of the spine with a size of approximately 15 cm×15 cm. The two test sites are located on the left cranial section and the right caudal section of the dorsal region. The two control sites are located on the left caudal and right cranial section of the dorsal region. FIG. 2 depicts the arrangement of test and control sites. The exposed skin is wiped with alcohol and dried. Rabbits of acceptable skin quality were selected and used for testing.

A 25×25 mm gauze patch saturated with 0.5 mL (liquid) or 0.5 g (powder) of Formulation 1 is applied to the clipped test sites. A 25×25 mm gauze patch saturated with 0.5 mL of 0.9% NaCl is used for the control and applied to the clipped control sites. The patches are secured using hypoallergenic, waterproof, surgical tape over the test and control sites. The animal's trunk is securely wrapped so as to maintain the position of the patches. Patches are left applied for a minimum of four hours.

After patch removal, the test and control sites were then scored for erythema and edema at 1, 24, 48 and 72 hours after patch removal. Only the 24, 48, and 72 hour observations were scored and used for calculations. The criteria for scoring is presented in Table 8. If no response was expected, testing was conducted using three animals per test article. If irritation was anticipated, one animal was tested initially. If the first animal received a score of 2 or less for either erythema or edema, 2 additional rabbits were used to conclude the test.

TABLE 8

Scoring Criteria for Test Reactions.

| Reaction | Description | Score |
|---|---|---|
| Erythema (ER) | No erythema | 0 |
| | Very slight (barely perceptible) | 1 |
| | Well defined | 2 |
| | Moderate | 3 |
| | Severe (beet-redness) to eschar formation preventing grading of erythema | 4 |
| Edema (ED) | No edema | 0 |
| | Very slight (barely perceptible) | 1 |
| | Well-defined edema (edges of area well-defined by definite raising | 2 |
| | Moderate (edges raised ~1 mm) | 3 |
| | Severe (raised more than 1 mm and extending beyond exposure area) | 4 |

For each animal and each extract, when applicable, the scores for the test article comprising Formulation Example 1 for erythema and edema at each time were added. This total was divided by the total number of observations. The same was done for the control sites. The control result was subtracted from the test results to give the irritation index for each animal. These scores for each animal were added and divided by the total number of animals to give the Primary Irritation Index. The Primary Irritation Index is depicted in Table 9. For any response, the Maximum Irritation Response, the time of onset of the response and the time of maximum response was recorded.

TABLE 9

Primary Irritation Index

| Primary Irritation Index | Response Category |
|---|---|
| 0-0.4 | Negligible |
| 0.5-1.9 | Slight |
| 2-4.9 | Moderate |
| 5-8 | Severe |

The results indicated that the skin reactions for both the test article comprising Formulation 1 and control samples were not significant. That data is presented in Table 10 below. Accordingly, the Formulation Example 1 is non-irritating.

TABLE 10

Direct Application of Test Article.

| | Formulation Example 1 | Control |
|---|---|---|
| Rabbit No. 14384 | ER + ED = Total<br>0 0 0<br>Test Total − Control Total = 0<br>Total Score Average = 0 | ER + ED = Total<br>0 0 0 | 
| Rabbit No. 14387 | ER + ED = Total<br>0 0 0<br>Test Total − Control Total = 0<br>Total Score Average = 0 | ER + ED = Total<br>0 0 0 |
| Rabbit No. 14394 | ER + ED = Total<br>0 0 0<br>Test Total − Control Total = 0<br>Total Score Average = 0 | ER + ED = Total<br>0 0 0 |

Total Average ( 0 ) = 0 Primary Irritation Index
No. of Animals ( 3 )

To positively validate the test, 10% sodium dodecyl sulfate (SDS), which is a known dermal irritant, in petroleum jelly was applied to a 2.5 cm×2.5 cm gauze patch. As a negative control, 0.5 mL of 0.9% NaCl was applied to a 2.5 cm×2.5 cm gauze patch. A Primary Irritation Index in the moderate to severe range is considered a positive result. The test system and methods utilized were the same as described above. Table 11 presents the results validating the study.

TABLE 11

Primary Skin Positive Validation Test.

| | 10% SDS | Control |
|---|---|---|
| Rabbit No. 14279 | ER + ED = Total<br>18 14 32<br>Test Total − Control Total = 32<br>Total Score Average = 5.3 | ER + ED = Total<br>0 0 0 |
| Rabbit No. 14280 | ER + ED = Total<br>21 19 40<br>Test Total − Control Total = 40<br>Total Score Average = 6.6 | ER + ED = Total<br>0 0 0 |
| Rabbit No. 14281 | ER + ED = Total<br>23 21 44<br>Test Total − Control Total = 44<br>Total Score Average = 7.3 | ER + ED = Total<br>0 0 0 |

Total Average ( 19.3 ) = 6.4 Primary Irritation Index
No. of Animals ( 3 )

Example 6. Suspension Time-Kill Procedure for MRSA, *T. rubrum*, and *Staphylococcus epidermidis*

A study was conducted to evaluate the changes in the population of MRSA in an antimicrobial liquid suspension comprising Formulation Example 1. Methicillin-resistant *Staphylococcus aureus* (MRSA) is a Gram-positive, cocci shaped, aerobe which is resistant to the penicillin-derivative antibiotic methicillin. MRSA can cause troublesome infections, and their rapid reproduction and resistance to antibiotics makes them more difficult to treat. MRSA bacteria are resistant to drying and can therefore survive on surfaces and fabrics for an extended period of time and therefore makes this bacteria an excellent representative for antimicrobial efficacy testing on surfaces.

To conduct the study, MRSA was prepared in liquid culture medium (Letheen Broth). The suspension of MRSA was standardized by dilution to $10^6$ in a buffered saline solution. Formulation 1 and control substance (PBS) were dispensed in identical volumes to sterile vessels. Independently, Formulation 1 and control substance were each inoculated with MRSA, then mixed and incubated. Control substances were immediately harvested and represented the concentration present at the start at the test (i.e. time zero). At the conclusion of contact time, a volume of the liquid test product was harvested and chemically neutralized. Dilutions of the neutralized test solution were assayed using appropriate growth media to determine the surviving MRSA at the respective contact times. Reductions in MRSA were calculated by comparing initial microbial concentrations to final microbial concentrations. Table 12 and FIG. 3 present the results of the study.

TABLE 12

Results of Suspension Time-Kill Test for MRSA (33592)

| Test substance | Contact time | Replicate | Replicate CFU/ml* | Average CFU/ml | Percent Reduction vs. Control at Time Zero | $Log_{10}$ Reduction vs. Control at Time Zero |
|---|---|---|---|---|---|---|
| PBS | Time Zero | 1 | 1.75E+06 | 1.48E+06 | N/A | |
| | | 2 | 1.20E+06 | | | |
| Formulation 1 | 30 seconds | 1 | 1.00E+01 | <1.00E+01 | >99.9993% | >5.17 |
| | | 2 | <1.00E+01 | | | |
| | 2 minutes | 1 | 1.00E+01 | <1.00E+01 | >99.9993% | >5.17 |
| | | 2 | <1.00E+01 | | | |

*The limit of detection for the assay is 1.00E+01 CFU/ml. Values below the limit of detection are notes as <1.00E+01 in the table.

The same study was conducted with *Trichophyton rubrum*. *T. rubrum* is a fungus which belongs to the dermatophyte group. Dermatophytes commonly cause skin disease in animals and humans. *T. rubrum* is anthropophilic, meaning it preferentially infects humans over animals. This parasite is the most common cause of fungal infection of the fingernail and Athlete's foot, this specific strain was isolated from a human toenail. In the laboratory, visible colonies can be observed after approximately 4-5 days and are fluffy and white in appearance. *T. rubrum* is a popular test microorganism for fungicidal testing, especially for products intended for use in environments where skin infections can occurs and spread rapidly such as locker rooms and schools.

To conduct the study, *T. rubrum* was prepared on agar (potato dextrose agar). The *T. rubrum* was resuspended and inoculated at a dilution of ~$10^6$ into vessels containing Formulation 1 and control substance (PBS). Control substances were immediately harvested and represented the concentration present at the start at the test (i.e. time zero). At the conclusion of contact time (2 or 10 minutes), a volume of the liquid test product was harvested and chemically neutralized. Dilutions of the neutralized test solution were assayed using appropriate growth media to determine the surviving *T. rubrum* at the respective contact times. Reductions in *T. rubrum* were calculated by comparing initial microbial concentrations to final microbial concentrations. Table 13 and FIG. 4 present the results of the study.

TABLE 13

Results of Suspension Time-Kill Test for *T. rubrum* (MYA-4438)

| Test substance | Contact time | Replicate | Replicate CFU/ml* | Average CFU/ml | Percent Reduction vs. Control at Time Zero | $Log_{10}$ Reduction vs. Control at Time Zero |
|---|---|---|---|---|---|---|
| PBS | Time Zero | 1 | 2.55E+05 | 3.15E+05 | N/A | |
| | | 2 | 3.75E+05 | | | |
| Formulation 1 | 2 minutes | 1 | 3.50E+03 | 2.18E+03 | 99.31% | 2.16 |
| | | 2 | 8.50E+02 | | | |
| | 10 minutes | 1 | <5.00E+01 | <5.00E+01 | >99.98% | >3.80 |
| | | 2 | 5.00E+01 | | | |

*The limit of detection for the assay is 5.00E+01 CFU/ml. Values elow the limit of detection are notes as <5.00E+01 in the table.

The same study was conducted with *Staphylococcus epidermidis*. Gram-positive organisms currently account for 50-60% of nosocomial bacteremic events. *Staphylococcus epidermidis* is the most common gram-positive organism isolated from blood (30% of isolates) and accounts for the majority of infections that are associated with intravascular catheters, as it is capable of forming antibiotic resistant biofilms on plastic surfaces.

In an effort to further explore the preventative benefits of Formulation Example 1 in preventing catheter related and hospital acquired infections, a suspension time kill assay as described above was initiated on this often under-discussed organism. A nearly 7 log kill over 24 hours was observed, which represents a typical change interval for intravenous catheter dressings (Table 14).

TABLE 14

Results of Suspension Time-Kill Test for *S. epidermidis* (ATCC 12228)

| Test substance | Contact time | Replicate CFU/ml* | Percent Reduction vs. Control at Time Zero | Logio Reduction vs. Control at Time Zero |
|---|---|---|---|---|
| PBS | Time Zero | 4.80E+06 | N/A | |
| Formulation 1 | 24 Hours | <1.00E+00 | >99.99998% | >6.68 |

The limit of detection is 1.00E+00 and is represented as <1.00E+00.

Example 7. The Use of Formulation Example 1 in a Slow Healing Wound Complicated by Patient Non-Compliance: Case Report A 56-year-old black male presented to clinic with the chief complaint of venous ulcers of right dorsal and plantar surfaces of foot and 2nd and 3rd toes. He had a prior medical history significant for chronic lymphedema, DM, HTN, Hyperlipidemia, CVA with residual hemiparesis of right side, wheelchair bound, tobacco dependence, seizure disorder, depression and asthma. He had been treated in the past with butadiene gauze wraps and iodasorb with kling, ace, and coban wraps with little improvement. Wound care was delivered twice weekly.

The patient received Clindamycin 300 TID×7 days due to the markedly minimal improvement of wound status over the first 7 weeks of treatment. Minimal improvement was noted after the antibiotic course.

Formulation Example 1 was utilized for the first time. A thin layer was applied to affected limb and ulcerations. The limb was dressed with gauze and coban in a compression wrap with weekly dressing changes to follow in this manner. Twenty-one days later significant improvement in wound appearance was observed and the wound on dorsal surface of the right foot had resolved completely. By four weeks, the entire dorsal surface was resolved and wounds were limited to plantar surface of the right 2nd and 3rd toes. By two months, wounds on plantar surfaces of the right foot were very defined and without any maceration. By three months, wounds had become essentially dry eschars with all tissues fully epithelialized.

In summary, all previous attempts to treat the patient's extensive wounds had failed but the introduction of Formulation 1 to the treatment marked a significant turning point in his care. Even in the face of extensive non-compliance and extended dressing change intervals, Formulation 1 remained in contact with the wound and continued to manage the environment.

Example 8. Use of Formulation Example 1 in Patient with History of Delayed Healing: Case Report A 76-year-old white female presented to clinic 24 hours after sustaining a 1.0×5.0×0.1 mm laceration to her right shin. She relates that she was standing near a wood pile when some wood fell and cut her. Radiographs were negative for fracture and ultrasound found no evidence of retained foreign body. The wound did not probe to bone. Her tetanus status was brought up to date. The wound was cleaned with sterile saline, edges re-approximated, and closed with retaining sutures and simple closure sutures in local ER.

Patient's medical history was significant for diabetes mellitus type 2 insulin dependent, CKD-4, ASCVD, and CABG-4 vessel. Notably, she relates a history of poor and delayed wound healing from graph site of right lower limb which took over 3 months to heal. She also suffers from peripheral neuropathy HTN, hyperlipidemia, obesity, and PVD/PAD.

Patient was seen in clinic and expressed concerns due to her history of delayed healing. Formulation 1 was applied with a standard dry, sterile dressing. Patient was instructed to return weekly for dressing changes.

The simple sutures were removed 2 weeks later. The wound showed no signs of dehiscence or infection. Edges were well approximated and surrounding tissue was appropriate to temperature and color. Formulation 1 continued to be used exclusively.

Retaining sutures were removed a week later. The wound was showing progressing epithelialization and had significantly decreased in size. The wound was dressed with Band-Aid and Formulation 1 for home use until completely healed.

By week 4, the patient was healed. There were no issues with wound healing or closure in a patient who had previously taken 12 weeks to heal from a saphenous graph harvest site. No revascularization had been done nor had any other health factor changed since the graft. This indicates that the use of Formulation 1 played an integral role in the closure of this wound.

The only factor that was changed in the patient's wound care for this laceration was the introduction of topical Formulation 1. With use of this product, the patient showed no signs of delayed healing. Her wound granulated and epithelialized as would be expected of a person without multiple systemic diseases. Formulation 1 appeared to have facilitated non-delayed healing while keeping the wound environment moist without macerating. Additionally, Formulation 1 stayed in contact with the wound and effective for a week without requiring dressing change, which is a benefit for patients with limited resources and transportation difficulties.

Example 9. Postoperative Treatment *Streptococcus* B Perianal Abscess with Formulation Example 1: Case Report A 51-year-old woman was admitted for the management of a perianal abscess. The patient had a history of a prior perianal abscess 6 months previously and an iodine allergy. The prior abscess had been treated via bedside I&D and oral antibiotics. With the recurrence of infection, concern for the presence of an anal fistula arose and the patient was admitted under SIRS criteria for evaluation and intervention.

Parenteral antibiotics were initiated, she was taken to the operating room for definitive treatment and placed under MAC anesthesia. An I&D was performed and exploration of the perianal space revealed a transsphincteric fistula as the source of the infection. A seton was initially placed to delineate the fistula. The fistula was subsequently repaired after the abscess was drained and washed out. Post-operatively a 3.3 cm deep soft tissue deficit remained.

In light of the patient's iodine allergy, the wound could not be treated with the standard betadine treated packing strips. Instead, the wound was packed with plain packing strips treated with Formulation 1, gauze, and sealed with Tegaderm. The patient was discharged on oral antibiotics with instructions for daily dressing changes to be performed.

Daily packing changes with the Formulation 1-treated packing strips were performed. By day 10 the soft tissue defect had fully granulated and packing was discontinued. The wound was subsequently dressed with a thin layer of Formulation 1 applied to the peri-wound area, with gauze and Tegaderm to seal the peripheral edges. By day 17 wound closure had been achieved.

The rate of granulation was markedly improved with the use of Formulation 1 when compared with the rates of healing with betadine packing strips. Typical rates with betadine strips run in the 4-6-week range. The difference in the rate of granulation is attributed to the difference in cytotoxic properties of the two products. Betadine, while being bactericidal, is also cytotoxic to fibroblasts which delays healing. Formulation 1 combines bactericidal properties with non-cytotoxicity to allow a more ideal environment for healing.

This case highlights the importance using of a non-cytotoxic, anti-microbial packing in the treatment of post-operative wounds. Ultimately, shorter duration of healing reduces the likelihood of opportunistic post-op infection and the use of a topical anti-microbial as an adjunctive treatment in conjunction with oral antibiotics provides a more ideal setting for healing to take place.

Example 10. The Use of Formulation 1 in the Treatment of Severe Abrasions: Case Report A 22-year old healthy male with no comorbidities was admitted to the emergency room with 2nd degree abrasions secondary to a locker room injury. Patient's tetanus status was addressed and wounds were cleaned and dressed with triple-antibiotic ointment, sterile gauze, and impregnated silver mesh. Patient and his parents were instructed to continue this dressing course BID upon release.

Five days post-hospitalization saw no visible reduction in wound state. Patient expressed distress over necrosis formation at the site and a 5/10 pain level. A trial of Formulation 1 with sterile gauze and paper tape was initiated at this point.

The wound was flushed with sterile saline, blotted dry, and a thin layer of Formulation 1 was applied topically to the wound bed and surrounding tissue. Wound dressing consisted of sterile gauze, kerlix, and paper tape. Patient was instructed to continue dressing changes BID, in the manner described.

By day 3 of treatment with Formulation 1, the wound had visibly improved. The eschar had autolytically debrided and the wound profile showed granular bases with well demarcated borders and the formation of skin islands. Patient reported a reduction of pain to 2/10.

After 10 days of dressing changes utilizing Formulation 1, the epithelial layer of skin had regenerated peripherally with mild central eschars at the central aspect of the wound bases. Pain was eliminated. Patient was able to resume normal activity at 10 days.

A rapid rate of healing, pain reduction, and elimination of necrotic tissue without requiring active debridement was achieved using Formulation 1. This dressing change protocol was significantly more economically effective than advanced impregnated dressings, while providing an appropriate environment for epithelization of the wound bed.

Example 11. The Use of Formulation 1 in the Treatment of Lower Leg Ulceration: Case Report A 70-year-old white man with a history of long-term smoking and DVT progressed to PE. Hospital course involved anticoagulation and IVF placement. Post-hospitalization, he developed bilateral lower leg venous ulcers and a low albumin level was diagnosed. Protein supplement was started along with aggressive dressing changes with honey sheets, unna boot, coban, and ace wrap performed twice a week progressing to weekly. Podiatry followed him twice a month for the acute phase. Albumin level normalized, dressing changes were continued with slow improvement, at which time acceptable healing had resulted and the patient was transitioned to compression stockings.

After one month of not wearing compression stockings, not elevating his extremities, and continuing to smoke, the patient developed a right lower leg ulcer. Given his history of slow healing, a trial of Formulation 1 was initiated. His albumin continued to be normal.

A thin layer of Formulation 1 was applied to and around the ulcer. A honey sheet was then applied followed by an unna boot, coban, and an ace wrap (for compression). This dressing was changed weekly. At each dressing change his leg was cleaned with saline.

After 4 weeks of weekly dressing changes utilizing Formulation 1, the ulcer was significantly smaller versus his prior history of slow healing. He transitioned back to compression stockings much faster.

A significant reduction in healing time was observed by including Formulation 1 versus not using Formulation 1 on this gentleman. His first ulcer was very slow to heal with the honey-only protocol (6-7 months); however, the addition of Formulation 1 with the same dressing technique on a second venous ulceration resulted in a dramatic reduction in healing time.

Example 12. The Use of Formulation Example 1 in the Treatment of a Pediatric Polymicrobial Infection: Case Report A 9-year-old boy with no significant medical history presented to clinic with an infected lesion to the left lateral chin. His father reports that the boy sustained a mechanical excoriation burn during karate when he fell on a mat. The parents treated the wound topically with bacitracin for 7 days and have noted a worsening of the erythema, edema, and topical warmth to the area with mild purulent drainage. The patient complained of tenderness to palpation. A culture, taken in office, revealed Herpes simplex type 1 and Methicillin Resistant *Staphylococcus aureus* (MRSA).

The patient was treated topically with Formulation Example 1. The patient's parents were instructed to wash the area gently with water and pat dry. The use of gloves was suggested due to the highly contagious nature of the infecting microorganisms. A thin layer of Formulation Example 1 was applied twice daily, morning and bedtime, and covered with a Band-Aid. The patient was given strict instructions to refrain from all sports until the infection abated.

The patient's parents reported by day two they the purulent drainage had ceased. The erythema and edema were resolving. By day 3 all edema and erythema had completely resolved. The patient was no longer tender to palpation. By day 7, the infection had completely resolved and the remaining eschar was beginning to loosen from the new epithelium.

The use of Formulation Example 1 is safe and effective for use on pediatric patient with polymicrobial skin infections. The petrol base is gentle on young skin and treats complicated infections. The ease of use is of particular importance in a pediatric population where swallowing medicines is often a challenge for caregivers. The aggressive treatment of infection in these highly communicable bacterial strains is an attractive feature of this product.

Example 13. The Use of Formulation Example 1 in the Treatment of Diaper Dermatitis: Case Report Irritant diaper dermatitis is a pervasive form of skin irritation commonly found in infants and toddlers. Prolonged exposure of the skin to irritants exacerbates these attacks. Such irritants include infrequent diaper changes, diarrhea, and contact allergy. The change in topical skin pH causes a breakdown in the epidermis, resulting in a painful erythematous rash to the most prominent areas of the buttocks.

The 4-month old patient was brought to his pediatrician by his parents after an acute onset of irritant diaper dermatitis. The patient exhibited a distressed affect, crying and avoiding pressure to the affect area. Upon physical exam, shiny erythematous raised patches were observed on the convex areas of the buttocks. Skin folds were spared. Parents reported that the rash has been present for 3 days and was worsening. Increased frequency in diaper changes had failed to improve symptoms. The patient had recently been experiencing diarrhea prior to onset which has now subsided.

The patient was assessed and the site of irritation was gently flushed with sterile water. The area was blotted dry and treated with topical application of Formulation Example 1 to the affected areas and surrounding tissue. A dry diaper was applied and the parents were given instructions for frequent diaper changes with gentle cleaning and application of Formulation Example 1 at each change.

Upon application the patient was noticeably more comfortable; the crying stopped and the patient began showing interest is a toy, indicating that the pain was subsiding. Twelve hours after the initial treatment the erythema had decreased by 85% and the parents reported that the child had resumed eating, playing, and was no longer fussy. After 18 hours a total resolution of the condition had been achieved.

The stratum corneum, the most superficial layer of skin, is comprised of keratinocytes and is thinner and especially sensitive in young pediatric patients. The third layer, the stratum granulosum, is a lipid producing layer which provides a hydrophobic barrier to the lesser skin layers thus providing a protective barrier to the irritant therefore the irritation is primarily contained to the first two epidermal layers. Formulation Example 1 has a petrolatum base and is naturally hydrophobic, thereby mimicking the body's natural defense mechanism and speeding healing to the affected area. The antimicrobial properties support the immune system and protect against common infections associated with severe diaper rash.

There are many treatments for irritant diaper dermatitis, the most common of which include zinc based creams, titanium dioxide jellies, anti-fungals, antacids, and corn starch. Research shows that the creams, jellies, and antacids are only minimally effective without application of a petrol layer. Anti-fungals are effective if the cause of the irritation is fungal in nature and often takes a 7-day course to achieve resolution. Lastly, corn starch is thought to prevent chaffing which minimizes discomfort but does not provide rapid relief from symptoms. Formulation Example 1 is currently the only product which has a petrolatum base that balances the pH of the skin and is capable of treating a polymicrobial infection.

A rapid rate of healing and pain resolution was achieved using Formulation Example 1. By providing a lipid bilayer, Formulation Example 1 aids the body's natural defenses to protect skin from pH induced breakdown with a medicated, water proof barrier thus both treating and protecting the skin simultaneously.

Example 14. Treatment of Non-Healing Abrasion with Formulation Example 1: Case Report Evidenced based protocols for the treatment of radiodermatitis is scarce and research indications that hospital management of these cases lacks consistency. A literature review in 2010 concluded that there was insufficient evidence to advocate for any one therapeutic option. In addition, a previous study reported an 80-90% incidence of erythematous reactions and a 10-15% incidence of moist desquamation in patients undergoing radiation therapy indicating this condition is a prevalent side effect to radiation therapy. Here, a case of radiodermatitis in which treatment with Formulation Example 1 was performed is reported.

A 54-year-old female had a history of a soft tissue sarcoma which had been successfully treated with radiation therapy, but consequently suffered an E3 Radiation-Induced Skin Reaction Assessment Scale (RISRAS) type radiodermatitis to the lateral aspect of her right lower extremity.

At 52 years, she experienced increased right distal leg pain and was referred to an oncologist where she was found to have a soft tissue sarcoma. After successful treatment of the sarcoma, which included adjuvant radiotherapy, she presented to the office with a 15.4 cm by 8.8 cm painful, solitary, erythematous plaque to the distal right lateral lower extremity consistent with radiodermatitis.

The occurrence rate of radiodermatitis in patients that underwent radiotherapy has been reported to be as high as 46% in one study. Side effects of this treatment results in increased occurrence of local skin lesions with possible ulceration, pain, and risk of infection.

The patient reported having been previously treated with hyaluronidase-based cream, sucralfate cream, biafine cream, and mepitel but was still experiencing pain and was displeased with the physical aesthetic of the wound. A thin layer of Formulation Example 1 was applied to and around the affected area. The area was covered with sterile telfa, wrapped with kerlix, and paper tape, taking care to avoid placing adhesive directly in contact with the skin. This dressing was changed twice daily. At each dressing change, the wound was cleaned with sterile saline.

A noticeable reduction in the erythema could be seen after one application and by the end of one week the plaque was almost totally resolved with only mild patchy spotting remaining. Patient reported that her pain had resolved completely and she was pleased with her outcome. In conclusion, Formulation Example 1 was found to be efficacious in treating radiodermatitis rapidly with no toxicity or side effects. The treatment was also economically efficacious. In future, randomized control trials will be established for further observation of Formulation Example 1 in treating radiation burns.

Example 15. Treatment of Wagner Grade 2 Ulceration with Formulation Example 1: Case Report A 72 year old man with cardiovascular disease and well-controlled diabetes mellitis presented to the clinic with an ulcer that had been present for 6 months. The ulcer measured 3.2 cm×1.9 cm×0.2 cm and was staged as a Wagner grade 2. He was married with 3 adult children, did not smoke, drank alcohol socially, and had a family history of various endocrine disorders. He denied previous ulcerations and attributed his ulcer to "a bug bite." Past treatment of his wound had included betadine, silvadene, and hydrogel to the wound bed. At time of presentation, he was applying silvadene every other day with a dry, sterile dressing, but wound measurements indicated poor healing. His medications were metformin, clopidogrel, metroprolol, low dose aspirin, and simvastatin with allergies to ACE inhibitors, penicillin, and sulfa drugs.

The patient presented for assessment of his diabetic ulcers and was found to have an ulcer on the lateral aspect of his calf. The wound base was 40:60 ratio fibrogranular with erythematous borders that extended 6 mm from the wound bed. Surrounding flesh was warm to the touch when compared to the contralateral side. It did not probe to bone, had no tracking, and exudate was moderate. A wound culture grew *Staphylococcus aureus* and pain was reported as 6/10.

Treatment began with mechanical debridement. Wound base was brought to bleeding and a thin layer of Formulation Example 1 was applied to the ulcer and surrounding tissue. The wound was dressed with a FiltreX bandage and this dressing was left in contact with the wound for 5 days. The patient was permitted to bathe while the FiltreX was in place, as it provides moisture protection. At day five, the home health nurse reported significant granulation and a reduction in the wound size from 3.2 cm×1.9 cm×0.2 cm to 2.1 cm×0.9 cm×0.05 cm.

Ten days into treatment revealed significant epithelialization of the wound bed. The wound measured 1.3 cm×0.4 cm.

Depth was no longer measureable as the surrounding tissue had granulated in. The patient reported no further pain, erythema had resolved, and temperature returned to appropriate, indicating a resolution of the inciting infection. Dressing with Formulation Example 1 and FiltreX was continued for 10 more days at which time the wound was found to be completely resolved with full epithelialization of the wound and the formation of fibrous tissue.

Formulation Example 1 is an adjunctive therapy for chronic diabetic ulceration. The petrolatum base provides the moisture necessary for proper wound healing without macerating the wound. Furthermore, the non-cytotoxic, antimicrobial properties are conducive to rapid healing in that it allows for unimpeded fibroblastic activity to take place, thereby creating an ideal setting for the body's natural response to wound healing.

With respect to comfort, affordability, and ease of use, Formulation Example 1 was found to be the ideal treatment formula. The bandage, and subsequently Formulation Example 1, stays in contact with the wound for up to 7 days. This dressing endurance, both primary and secondary, is unique and minimizes the need for daily interruptions of the patient's life for dressing changes. Additionally, the bandage is hydrophobic which ensures the patient may bathe without concerns of dressing or wound disruption. This is a unique advantage due to the ability to shower making treatment more tolerable. In terms of patient compliance, the comfort and versatility of this dressing combination increases the likelihood that the patient will maintain a proper healing environment thereby leading to more successful outcomes. Ultimately, the combination of Formulation Example 1 and FiltreX provided the ideal environment for complete resolution of this difficult to heal diabetic ulcer.

Example 16. Treatment of Non-Healing Complicated Skin Tear with Formulation Example 1: Case Report Skin tears result from a separation of the two major layers of human skin, the epidermis and the dermis. They represent a major problem affecting older adults with prevalence rates between 14% and 24%. An 88 year old white female with a history of Alzheimer's, low albumin, PVD, hypertension, and hypothyroidism had been undergoing unsuccessful treatment for four months in an attempt to manage a complicated skin tear. Many dressing techniques had been attempted with minimal progress, including silver and topical antibiotics. A thin layer of Formula I was applied to and around the wound area. A non-adherent gauze sheet was then applied, followed by an ace wrap (for compression). This dressing was changed weekly. At each dressing change, her leg was cleaned with saline. Within weeks, the wound had stabilized, with complete epithelialization within two weeks. Notable healing can be seen and continues through week eleven. Moreover, while non-adherent regimens were always used, dressing changes were painful to the patient, indicated by visual and auditory responses to the removal of dressing materials from the wound site. While using Formulation Example 1 there was no discomfort/pain response during dressing changes. Formulation Example 1 added an additional, non-adherent layer of protection, decreasing discomfort while stimulating healing, ultimately resulting in re-epithelialization The use of Formulation Example 1 during the dressing change protocol stimulated healing, protected the site from additional physical insult, and reduced pain during dressing changes. For such non-ambulatory patients, risk of limb loss and infection is very high, and the healing of such a complicated, difficult wound represents a major success.

Example 17. Treatment of Phytophotodermatitis with Formulation Example 1: Case Report A 38-year-old woman with no significant medical history presented with a 2-day history of an erythematous vesiculobullous plaque with localized edema and erythema. She denied puritis, but admitted to associated burning sensation. Prior to the onset of the lesion, she went hiking near her home during which she picked oranges off of a tree she found. Upon examination, the patient has a central plaque measuring 4.1 cm×3.4 cm with interspersed vesicles/bullae which the patient admitted to draining at home. There are 2 secondary patches: one measuring 0.9 cm and the other 4 mm. The lesions are located on the left anterior shin. They are edematous and erythematous, but without appreciable temperature variation as compared to the contralateral side.

Based on the patient's presentation and recent exposure to citrus plants, she was diagnosed with phytophotodermatitis, a common dermatological condition resulting from contact with furocoumarins under direct sunlight. The result of this exposure causes a phototoxic inflammatory response to the localized area. A common defining feature of this clinical condition is the absence of puritis with the patient complaining of burning instead, which differentiates this from contact dermatitis. There are four species of plants that are known to contain furocoumarins: Apiaceae, Rutaceae, Moraceae, and Leguminosae. Members of Apiaceae include parsnip, celery, and parsley. Rutaceae includes citrus fruits, and is thus the likely culprit in the present case. Figs belong to the Moraceae family and lastly, *Psoralea corylifolia* belongs in Leguminosae family.

The course of this condition begins with the acute phase, which peaks at day 3 and can last 3-5 days. The more concerning aspect of this condition, from the patient standpoint, is the resultant hyperpigmentation which often persists for years. This condition most commonly affects areas that are exposed to the element, such as hands, arms, and lower legs, so patients tend to be distressed over the resultant physical deformity.

A thin layer of Formulation Example 1 was applied to the plaque and surrounding tissues. The area was covered with sterile telfa, wrapped with kerlix and paper tape, taking care to avoid placing adhesive directly in contact with the skin. This dressing was changed daily. At each dressing change, the wound was cleaned with sterile saline.

After 3 days of application, the acute phase resolved and the post-inflammatory hyperpigmentation set in. The patient continued with daily dressing changes and by 20 days of treatment, the hyperpigmentation was almost totally resolved with only mild patchy spotting remaining.

Formulation Example 1 was found to be efficacious in treating both the acute and post-inflammatory hyperpigmentation phases of phytophotodermatitis, the latter of which is known to often persist for years. In the future, it is recommended that randomized control trials be conducted with Formulation Example 1 to treat hyperpigmented lesions.

Example 18. Stability

Formulation Example 1 was packaged in tubes was subjected to an accelerated stability study. Formulation Example 1 was placed sideways in a 40° C.±2° C./75%±5% relative humidity (RH) storage chamber for different intervals to yield a period of three months. The product was assessed for physical and analytical characteristics. When stored at 40° C.±2° C./75%±5% (RH) benzyl alkonium chloride was stable as shown in Table 15.

TABLE 15

Accelerated Stability Testing

| Analytical Assay Testing | Specification | Initial: Assessing | 1 Month Assessing | 2 Months Assessing | 3 Months Assessing |
|---|---|---|---|---|---|
| Benzalkonium Chloride 0.0081% | 0.0071%-0.0086% | 0.0084% | 0.0085% | 0.0075% | 0.0086% |

Additionally, the product met specification for appearance, odor, specific gravity, viscosity and package compatibility at all time points tested.

Formulation Example 1 was also tested under for microbial counts at 40° C.±2° C./75%±5% were as shown below. The results are shown in Table 16.

TABLE 16

Accelerated Stability Testing

| Micro Testing | SPEC | Method | Results Initial Assessing | 1 Month Assessing | 2 Months Assessing | 3 Months Assessing |
|---|---|---|---|---|---|---|
| Total Plate Count (TPC) | <100 cfu/ml | TM-01 | <10 cfu/ml | <10 cfu/ml | <10 cfu/ml | <10 cfu/ml |
| Yeast/Mold | <100 cfu/ml | TM-01 | <10 cfu/ml | <10 cfu/ml | <10 cfu/ml | <10 cfu/ml |
| Enrichment (Pathogens) | Absent | Absent | Absent | Absent | Absent | Absent |
| *Pseudomonas* | Absent | Absent | Absent | Absent | Absent | Absent |
| *S. aureus* | Absent | Absent | Absent | Absent | Absent | Absent |
| *E. coli* | Absent | Absent | Absent | Absent | Absent | Absent |
| *Coliforms* | Absent | Absent | Absent | Absent | Absent | Absent |
| *Salmonella Shigella* | Absent | Absent | Absent | Absent | Absent | Absent |

Additionally, the product met specification for appearance, odor, specific gravity, viscosity and package compatibility at all time-points tested when under standard conditions for over nine months.

Example 19. Effect of Formulation Example 1 on Bio-Burden in Live Wounds

Fresh wounds on eight patients were treated by applying a thin layer Formulation Example 1 to the wounds and surrounding tissue. The wounds were dressed with a pressure dressing, and this dressing was left in contact with the wound for one week. The wound was swabbed before treatment and then again at the conclusion of treatment when the dressing was removed after a week. Bio-burden analyses of the swab samples were performed for total microbial count and *Staphylococcus* count.

TABLE 17

Bio-burden analysis

| | Total Bacteria CFU/Swab | | *Staphylococcus* spp. CFU/Swab | |
|---|---|---|---|---|
| Sample ID | Pre | Post | Pre | Post |
| Patient 3 | $9.50 \times 10^3$ | $2.10 \times 10^2$ | $1.55 \times 10^4$ | <5.00 |
| Patient 4 | $3.40 \times 10^6$ | $1.87 \times 10^5$ | $2.70 \times 10^6$ | $2.15 \times 10^4$ |
| Patient 5 | $2.97 \times 10^5$ | 5.00 | $5.30 \times 10^2$ | <5.00 |
| Patient 6 | $5.50 \times 10^5$ | N/A | $3.51 \times 10^5$ | N/A |
| Patient 7 | $1.06 \times 10^7$ | $4.02 \times 10^5$ | $7.60 \times 10^6$ | $3.00 \times 10^5$ |
| Patient 8 | $6.32 \times 10^5$ | N/A | $2.60 \times 10^4$ | N/A |

TABLE 17-continued

Bio-burden analysis

| | Total Bacteria CFU/Swab | | *Staphylococcus* spp. CFU/Swab | |
|---|---|---|---|---|
| Sample ID | Pre | Post | Pre | Post |
| Patient 10 | $7.00 \times 10^6$ | N/A | $2.85 \times 10^4$ | N/A |
| Patient 11 | $3.25 \times 10^6$ | N/A | $1.60 \times 10^6$ | N/A |

The limit of detection for this assay was 5CFU/Swab.
The limit of detection for patient 3 was 10 CFU/Swab.
Samples with no microbial recovery are reported as <5.00.
Wounds that were completely healed within the seven day period were not swabbed after treatment and were marked N/A.

One week after treatment revealed significant reductions in total microbial counts and *Staphylococcus* counts. This was especially apparent for the *Staphylococcus* counts. In some instances, the wounds were healed within the seven day duration of the experiment, and therefore were not swabbed.

Example 20. Preparation of 50/50 Collagen Wound Care Composition (Formulation 2)

A 50/50 collagen wound care composition ("formulation 2") was prepared by mixing at room temperature Type-1 bovine powdered collagen obtained from Strukmyer (strukmyer.com) with formulation 1, the hydrophobic barrier/oil-based antimicrobial composition obtained in Example 1, such that the resultant collagen wound care composition comprised 50 weight percent powdered collagen and 50 weight percent hydrophobic barrier/oil-based antimicrobial composition (formulation 1).

Example 21. Preparation of 80/20 Collagen Wound Care Composition (Formulation 3)

A 80/20 collagen wound care composition ("formulation 3") was prepared by mixing at room temperature Type-1 bovine powdered collagen obtained from Strukmyer (strukmyer.com) with formulation 1, the hydrophobic barrier/oil-based antimicrobial composition obtained in Example 1, such that the resultant collagen wound care composition comprised 80 weight percent powdered collagen and 20 weight percent hydrophobic barrier/oil-based antimicrobial composition (formulation 1).

Example 22. Kill Rate Test Results for 50/50 Collagen Wound Care Composition (Formulation 2)

A kill rate test of the 50/50 collagen wound care composition (formulation 2) was conducted on 25 g of formulation 2 against *Escherichia coli* (ATCC No. 8739) and MRSA (ATCC No. 33591) at 8 hours, 16 hours, and 24 hours. The results are shown in Table 18. As shown in Table 18, formulation 2 is effective in killing *E. coli* and MRSA as demonstrated by the greater than 2 log reduction in colony forming units.

TABLE 18

Kill Rate Test Results for 50/50 Collagen Wound Care Composition (Formulation 2)

| Organisms | Inoculum (cfu/mL) | Average (cfu/g) | Log Reduction |
|---|---|---|---|
| E. coli 8 hours | $7.98 \times 10^6$ | 7,500 | 3.03 |
| E. coli 16 hours | $8.43 \times 10^6$ | 45 | 5.27 |
| E. coli 24 hours | $7.98 \times 10^6$ | No Growth | 6.90 |
| MRSA 8 hours | $1.20 \times 10^7$ | 21,000 | 2.76 |
| MRSA 16 hours | $1.18 \times 10^7$ | 20,000 | 2.77 |
| MRSA 24 hours | $1.20 \times 10^7$ | 7,000 | 3.23 |

Example 23. Kill Rate Test Results for 80/20 Collagen Wound Care Composition (Formulation 3)

A kill rate test of the 80/20 collagen wound care composition (formulation 3) was conducted on 25 g of formulation 3 against *Escherichia coli* (ATCC No. 8739) and MRSA (ATCC No. 33591) at 8 hours, 16 hours, and 24 hours. The results are shown in Table 19. As shown in Table 19, formulation 3 is effective in killing *E. coli* and MRSA as demonstrated by the greater than 2 log reduction in colony forming units. It was surprisingly discovered that the 80 weight percent collagen formulation (formulation 3) exhibited significantly stronger kill rates as compared to the 50 weight percent collagen formulation (formulation 2), indicating that the increased collagen may provide additional surface area for adsorbed antimicrobial ingredients, thereby increasing availability of the antimicrobial agents to work against the test organisms.

TABLE 19

Kill Rate Test Results for 80/20 Collagen Wound Care Composition (Formulation 3)

| Organisms | Inoculum (cfu/mL) | Average (cfu/g) | Log Reduction |
|---|---|---|---|
| E. coli 8 hours | $7.98 \times 10^6$ | No Growth | 6.90 |
| E. coli 16 hours | $8.43 \times 10^6$ | No Growth | 6.93 |
| E. coli 24 hours | $7.98 \times 10^6$ | No Growth | 6.90 |
| MRSA 8 hours | $1.20 \times 10^7$ | 25 | 5.68 |
| MRSA 16 hours | $1.18 \times 10^7$ | No Growth | 7.07 |
| MRSA 24 hours | $1.20 \times 10^7$ | No Growth | 7.08 |

Example 24. Kill Rate Test Results for 80/20 Collagen Wound Care Composition (Formulation 3)

A kill rate test of the 80/20 collagen wound care composition (formulation 3) was conducted on 5 g of formulation 3 against *Staphylococcus aureus* (ATCC No. 6538) at 8 hours and 24 hours. The results are shown in Table 20. As shown in Table 20, formulation 3 is effective in killing *Staphylococcus aureus* as demonstrated by the greater than 2 log reduction in colony forming units at 24 hours.

TABLE 20

Kill Rate Test Results for 80/20 Collagen Wound Care Composition (Formulation 3)

| Organisms | Inoculum (cfu/mL) | Average (cfu/g) | Log Reduction |
|---|---|---|---|
| S. aureus 8 hours | $1.04 \times 10^6$ | 64,500 | 1.21 |
| S. aureus 24 hours | $1.04 \times 10^6$ | 40 | 4.41 |

Example 25. Kill Rate Test Results for 80/20 Collagen Wound Care Composition (Formulation 3)

A kill rate test of the 80/20 collagen wound care composition (formulation 3) was conducted on 10 g of formulation 3 against *Candida auris* (ATCC No. MYA-5001 (B11220)) at 8 hours and 24 hours. The results are shown in Table 21. As shown in Table 21, formulation 3 is effective in killing *Candida auris* as demonstrated by the greater than 2 log reduction in colony forming units at 8 and 24 hours.

TABLE 21

Kill Rate Test Results for 80/20 Collagen Wound Care Composition (Formulation 3)

| Organisms | Inoculum (cfu/mL) | Average (cfu/g) | Log Reduction |
|---|---|---|---|
| C. auris 8 hours | $1.11 \times 10^6$ | 50 | 4.35 |
| C. auris 24 hours | $1.11 \times 10^6$ | 35 | 4.50 |

Example 26. Kill Rate Test Results for 80/20 Collagen Wound Care Composition (Formulation 3)

A kill rate test of the 80/20 collagen wound care composition (formulation 3) was conducted on 20 g of formulation 3 against *Pseudomonas aeruginosa* (ATCC No. 9027), *Staphylococcus epidermidis* (ATCC No. 12228), Vancomycin-resistant *Enterococcus faecalis* (VRE) (ATCC No. 51575), and *Salmonella enterica* (ATCC No. 14028) at 8 hours and 24 hours. The results are shown in Table 22. As shown in Table 22, formulation 3 is effective in killing *Pseudomonas aeruginosa, Staphylococcus epidermidis*, Vancomycin-resistant *Enterococcus faecalis, Salmonella enterica*, as demonstrated by the greater than 2 log reduction in colony forming units at 8 and 24 hours.

TABLE 22

Kill Rate Test Results for 80/20 Collagen Wound Care Composition (Formulation 3)

| Organisms | Inoculum (cfu/mL) | Average (cfu/g) | Log Reduction |
|---|---|---|---|
| P. aeruginosa 8 hours | $1.24 \times 10^6$ | 125 | 4.00 |
| P. aeruginosa 24 hours | $1.24 \times 10^6$ | No Growth | 6.09 |
| S. epidermidis 8 hours | $1.28 \times 10^6$ | 10 | 5.11 |
| S. epidermidis 24 hours | $1.28 \times 10^6$ | No Growth | 6.11 |
| VRE 8 hours | $2.49 \times 10^6$ | 1,658 | 2.97 |
| VRE 24 hours | $2.49 \times 10^6$ | 335 | 3.87 |
| S. enterica 8 hours | $1.42 \times 10^6$ | No Growth | 6.15 |
| S. enterica 24 hours | $1.42 \times 10^6$ | No Growth | 6.15 |

Example 27: Cytotoxicity Evaluation of Formulation 3 Using the ISO Direct Contact Method Formulation 3 was evaluated to determine the potential for cytotoxicity. This study was conducted based on the requirement of ISO 10993-5, Biological evaluation of medical devices—Part 5: Tests for in vitro cytotoxicity. Culture wells of a 6-well tissue culture plate that contained a subconfluent monolayer of L-929 mouse fibroblast cells were used for testing. Triplicate wells were dosed with either a test article section, high density polyethylene as a negative control, 0.9% sodium chloride as a filter disc control, or latex as a positive control. Each article was placed in direct contact with the L-929 cells. After incubating for 24-26 hours, the cultures were examined microscopically (100×) for any abnormal cell morphology and cell lysis in proximity to the articles.

Formulation 3 showed evidence of causing mild cell lysis or cytotoxicity to L-929 cells. The test article met the requirements of the test since the grade was equal to a grade 2 (mild reactivity). Scores for cytotoxicity was based on the criteria provided in Table 23.

TABLE 23

Grading Guidelines.

| Grade | Reactivity | Description of the Reactivity Zone |
|---|---|---|
| 0 | None | No detectable zone around or under specimen |
| 1 | Slight | Some malformed or degenerated cells under specimen |
| 2 | Mild | Zone limited to area under specimen |
| 3 | Moderate | Zone extending specimen size up to 1.0 cm |
| 4 | Severe | Zone extends greater than 1.0 cm beyond specimen |

For the suitability of the system to be confirmed, the negative control and filter disc control must have been a grade of 0 (reactivity none) and the positive control must have produced a zone of lysis for a grade equal to or greater than a grade of 3 (reactivity moderate to severe). The test article met the requirements of the test if all three monolayers exposed to the test article showed cytotoxicity no greater than a grade of 2 (reactivity mild).

Table 24 depicts the results of the study. Formulation 3 showed evidence of causing mild cell lysis or cytotoxicity to L-929 cells. Formulation 3 met the requirements of the test since the grade was equal to a grade 2 (mild reactivity).

TABLE 24

Cytotoxicity Test Results

| Test/Control Articles | Zone of Lysis (mm) | Lysis Under Article | Grade | Reactivity |
|---|---|---|---|---|
| Formulation 3-Replicate 1 | 0 | Complete | 2 | Mild |
| Formulation 3-Replicate 2 | 0 | Complete | 2 | Mild |
| Formulation 3-Replicate 3 | 0 | Complete | 2 | Mild |
| Filter Disc Control-Replicate 1 | 0 | None | 0 | None |
| Filter Disc Control-Replicate 2 | 0 | None | 0 | None |
| Filter Disc Control-Replicate 3 | 0 | None | 0 | None |
| Negative Control-Replicate 1 | 0 | None | 0 | None |
| Negative Control-Replicate 2 | 0 | None | 0 | None |
| Negative Control-Replicate 3 | 0 | None | 0 | None |
| Positive Control-Replicate 1 | 11 | Complete | 4 | Severe |
| Positive Control-Replicate 2 | 11 | Complete | 4 | Severe |
| Positive Control-Replicate 3 | 12 | Complete | 4 | Severe |

Statements of the Disclosure

Statement 1: A collagen wound care composition, the composition comprising: powdered collagen or collagen-based material, the powdered collagen or collagen-based material substantially covered with a hydrophobic barrier.

Statement 2: The composition according to Statement 1, wherein the hydrophobic barrier prevents the complete absorption of the powdered collagen or collagen-based material when placed on or in a wound or body of a subject for at least three (3) days.

Statement 3: The composition according to Statement 2, wherein the wound and/or one or more tissues surrounding the wound is characterized as having a good blood supply.

Statement 4: The composition according to any one of Statements 1-3, wherein the hydrophobic barrier prevents the complete absorption of the powdered collagen or collagen-based material when placed on or in a wound or body of a subject for at least seven (7) days.

Statement 5: The composition according to any one of Statements 1-4, wherein the hydrophobic barrier prevents the dissolution of the powdered collagen or collagen-based material when placed on or in a wound or body of a subject for at least three (3) days.

Statement 6: The composition according to any one of Statements 1-4, wherein the hydrophobic barrier prevents the dissolution of the powdered collagen or collagen-based material when placed on or in a wound or body of a subject for at least seven (7) days.

Statement 7: The composition according to any one of Statements 1-6, wherein the hydrophobic barrier is at least partially adsorbed to the surface of the powdered collagen or collagen-based material.

Statement 8: The composition according to any one of Statements 1-6, wherein the hydrophobic barrier at least partially coats the surface of the powdered collagen or collagen-based material.

Statement 9: The composition according to any one of Statements 1-6, wherein the hydrophobic barrier substantially coats the powdered collagen or collagen-based material.

Statement 10: The composition according to any one of Statements 1-6, wherein the hydrophobic barrier forms a coat on the powdered collagen or collagen-based material.

Statement 11: The composition according to any one of Statements 1-6, wherein the powdered collagen or collagen-based material is coated with the hydrophobic barrier.

Statement 12: The composition according to any one of Statements 1-6, wherein the powdered collagen or collagen-based material comprises a plurality of particles comprising collagen or collagen-based material.

Statement 13: The composition according to Statement 12, wherein the plurality of particles are at least partially coated with the hydrophobic barrier.

Statement 14: The composition according to Statement 12, wherein the plurality of particles are substantially coated with the hydrophobic barrier.

Statement 15: The composition according to Statement 12, wherein the hydrophobic barrier is at least partially adsorbed to the surface of the plurality of particles.

Statement 16: The composition according to any one of Statements 1-15, wherein the hydrophobic barrier comprises one or more oils.

Statement 17: The composition according to Statement 16, wherein the one or more oils is selected from the group consisting of animal oil, vegetable oil, natural oil, synthetic oil, hydrocarbon oils, silicone oils, and semi-synthetic derivatives thereof, and any combination thereof.

Statement 18: The composition according to Statement 16, wherein the one or more oils is selected from the group consisting of mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, C12-15 alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*Simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combination thereof.

Statement 19: The composition according to Statement 16, wherein the one or more oils is coconut oil.

Statement 20: The composition according to Statement 16, wherein the one or more oils is petrolatum.

Statement 21: The composition according to Statement 16, wherein the one or more oils comprises greater than about 80% by weight petrolatum.

Statement 22: The composition according to any one of Statements 1-21, wherein the hydrophobic barrier comprises greater than about 80% by weight petrolatum.

Statement 23: The composition according to Statements 16-22, wherein the hydrophobic barrier comprises greater than about 80% by weight oil.

Statement 24: The composition according to any one of Statements 1-23, wherein the hydrophobic barrier comprises one or more preservatives.

Statement 25: The composition according to any one of Statements 1-24, wherein the one or more preservatives is selected from the group consisting of polyhexamethylene biguanide (PHMB), polyaminopropyl biguanide (PAPB), benzalkonium chloride, cetrimide, chlorhexidine, polihexanide biguanide, polihexanide, polyhexamethylene guanide, poly(iminoimidocarbonyl-iminoimidocarbonyl-iminohexamethylene), and any salt or combination thereof.

Statement 26: The composition according to any one of Statements 1-24, wherein the one or more preservatives comprises polyhexamethylene biguanide (PHMB).

Statement 27: The composition according to Statement 26, wherein the hydrophobic barrier comprises from about 0.05% to about 5% by weight PHMB.

Statement 28: The composition according to any one of Statements 1-24, wherein the one or more preservatives comprises a cationic biocide.

Statement 29: The composition according to any one of Statements 1-24, wherein the one or more preservatives is selected from the group consisting of benzalkonium chloride, cetrimide, chlorhexidine, and any salt or combination thereof.

Statement 30: The composition according to any one of Statements 1-29, wherein the hydrophobic barrier comprises from about 0.001% to about 0.15% by weight benzalkonium chloride (BZK).

Statement 31: The composition according to any one of Statements 1-30, wherein the hydrophobic barrier comprises from about 0.05% to about 5% by weight PAPB.

Statement 32: The composition according to any one of Statements 1-30, wherein the hydrophobic barrier comprises from about 0.001% to about 5% by weight of the one or more preservatives.

Statement 33: The composition according to any one of Statements 1-32, wherein the powdered collagen or collagen-based material comprises from about 45 weight percent to about 85 weight percent of the collagen wound care composition.

Statement 34: The composition according to any one of Statements 1-33, wherein the hydrophobic barrier comprises from about 15 weight percent to about 55 weight percent of the collagen wound care composition.

Statement 35: The composition according to any one of Statements 1-34, wherein the hydrophobic barrier comprises a polar solvent, the polar solvent suspended in the hydrophobic barrier and comprising one or more preservatives.

Statement 36: The composition according to any one of Statements 1-35, wherein the collagen wound care composition has a fluffy or unconsolidated consistency suitable for wound packing.

Statement 37: The composition according to any one of Statements 1-36, wherein the collagen wound care composition comprises from about 50 weight percent to about 80 weight percent powdered collagen or collagen-based material.

Statement 38: The composition according to any one of Statements 1-36, wherein the collagen wound care composition comprises from about 60 weight percent to about 80 weight percent powdered collagen or collagen-based material.

Statement 39: The composition according to any one of Statements 1-36, wherein the collagen wound care composition comprises from about 65 weight percent to about 85 weight percent powdered collagen or collagen-based material.

Statement 40: The composition according to any one of Statements 1-36, wherein the collagen wound care composition comprises from about 75 weight percent to about 85 weight percent powdered collagen or collagen-based material.

Statement 41: The composition according to any one of Statements 1-40, wherein the collagen wound care composition comprises from about 20 weight percent to about 50 weight percent hydrophobic barrier.

Statement 42: The composition according to any one of Statements 1-40, wherein the collagen wound care composition comprises from about 20 weight percent to about 40 weight percent hydrophobic barrier.

Statement 43: The composition according to any one of Statements 1-40, wherein the collagen wound care composition comprises from about 15 weight percent to about 35 weight percent hydrophobic barrier.

Statement 44: The composition according to any one of Statements 1-40, wherein the collagen wound care composition comprises from about 15 weight percent to about 25 weight percent hydrophobic barrier.

Statement 45: The composition according to any one of Statements 1-44, wherein the hydrophobic barrier does not separate from the collagen or collagen-based material for at least 6 months.

Statement 46: The composition according to any one of Statements 1-45, wherein the polar solvent comprising one or more preservatives does not separate from the hydrophobic barrier for at least 6 months.

Statement 47: The composition according to any one of Statements 1-46, wherein the powdered collagen or collagen-based material is characterized by an average particle size of from about 5 microns to about 80 microns.

Statement 48: The composition according to any one of Statements 1-47, wherein the powdered collagen or collagen-based material is prepared with a pH under 4.

Statement 49: The composition according to any one of Statements 1-47, wherein the powdered collagen or collagen-based material comprises a pH under 4.

Statement 50: The composition according to any one of Statements 1-49, wherein the powdered collagen or collagen-based material is bovine collagen or collagen obtained from a bovine.

Statement 51: The composition according to any one of Statements 1-50, wherein the powdered collagen or collagen-based material is Type-1 bovine collagen.

Statement 52: The composition according to any one of Statements 1-51, where in the powdered collagen or collagen-based material comprises a material selected from the group consisting of extracellular matrix materials, micronized extracellular matrix, purified collagen, Type I collagen, Type II collagen, Type III collagen, Type X collagen, collagen fibers, collagen fibrils, micronized collagen, defibrillated collagen, coarse collagen bundles, non-crosslinked collagen, non-mineralized collage, collagen treated to control cross-linking (e.g., via chemical, thermal, photo, or radiation-induced cross-linking), collagen-glycosaminoglycan (GAG) mixtures, and any combination thereof.

Statement 53: The composition according to any one of Statements 1-52, wherein the polar solvent is selected from the group consisting of water, ethanol, a mixture of water and ethanol, acetic acid, and any combination thereof.

Statement 54: The composition according to any one of Statements 1-53, wherein the hydrophobic barrier excludes an added emulsifier other than the recited components.

Statement 55: The composition according to any one of Statements 1-54, wherein the composition is a fluffy powdered collagen matrix or a collagen gel for application to the wound of a subject in need thereof.

Statement 56: The composition according to any one of Statements 1-55, wherein the collagen wound care composition is prepared by mixing the powdered collagen or collagen-based material with the hydrophobic barrier without heating.

Statement 57: The composition according to any one of Statements 1-56, wherein the collagen wound care composition is prepared by mixing the powdered collagen or collagen-based material with the hydrophobic barrier at a temperature from about 0 degrees Celsius to about 25 degrees Celsius.

Statement 58: The composition according to any one of Statements 1-57, wherein the hydrophobic barrier is prepared by a process comprising: a) dissolving the one or more preservatives in a polar solvent to give a preservative solution; b) heating an oil to a temperature sufficient to cause the oil to melt or to a temperature sufficient to provide a oil having a density capable of suspending the polar solvent comprising one or more preservatives, resulting in a melted oil; c) heating the preservative solution to a temperature higher than the temperature of the melted oil to give a heated preservative solution; e) mixing the melted oil and the heated preservative solution to give a melted mixture; and f) cooling the melted mixture to give the hydrophobic barrier.

Statement 59: The composition according to Statement 58, wherein the heated preservative solution has a temperature that is about 1° C. to about 5° C. higher than the temperature of the melted oil at the time of mixing.

Statement 60: A method of treating or dressing a wound or a post-surgical incision in a subject, the method comprising applying the composition according to any one of Statements 1-59 to a wound or post-surgical incision in need of dressing or treatment.

Statement 61: The method according to Statement 60, further comprising: contacting the composition according to any one of Statements 1-59 to a wound covering, wherein the wound covering is a selected from the group consisting of a bandage, wrap, gauze, sponge, and film; and applying the wound covering to the wound or post-surgical skin graft in need of treatment.

Statement 62: The method according to Statement 60 or Statement 61, further comprising: packing the wound or post-surgical incision with the composition according to any one of Statements 1-59.

Statement 63: The method according to Statement 62, further comprising: applying a wound covering to the packed wound or post-surgical incision.

Statement 64: A system for treating or dressing a wound or a post-surgical incision in a subject, the system comprising: a collagen wound care composition according to any one of Statements 1-59; and a wound covering; wherein the wound covering is operable to cover the wound once it is treated or packed with the collagen wound care composition.

Statement 65: A kit for treating or dressing a wound or a post-surgical incision in a subject, the kit comprising: a packaging containing a collagen wound care composition according to any one of Statements 1-59, wherein the packaging is selected from the group consisting of a screw-cap cylindrical tube or vial, a snap-cap cylindrical tube or vial, a screw-cap or snap-cap collapsible tube or squeeze tube, and any combination thereof.

Statement 66: A composition, method, system, or kit according to any one of Statements 1-65, wherein the collagen wound care composition is sterilized by e-beam radiation sterilization or gamma radiation sterilization.

Statement 67: A collagen wound care composition for the treatment or dressing of a wound, the composition comprising: from about 45 weight percent to about 85 weight percent collagen or collagen-based material; and from about 15 weight percent to about 55 weight percent oil-based antimicrobial composition, the oil-based antimicrobial composition at least partially adsorbed to the collagen-based material; wherein the oil-based antimicrobial composition comprises: an oil-based carrier; and a polar solvent comprising one or more polar antimicrobial agents, wherein the polar solvent comprising one or more polar antimicrobial agents is suspended in the oil-based carrier.

Statement 68: The composition according to Statement 67, wherein the collagen wound care composition has a fluffy or unconsolidated consistency suitable for wound packing.

Statement 69: The composition according to Statement 67 or Statement 68, wherein the collagen wound care composition comprises from about 50 weight percent to about 80 weight percent collagen or collagen-based material.

Statement 70: The composition according to any one of Statements 67-69 wherein the collagen wound care composition comprises from about 60 weight percent to about 80 weight percent collagen or collagen-based material.

Statement 71: The composition according to any one of Statements 67-69, wherein the collagen wound care composition comprises from about 65 weight percent to about 85 weight percent collagen or collagen-based material.

Statement 72: The composition according to any one of Statements 67-69, wherein the collagen wound care composition comprises from about 75 weight percent to about 85 weight percent collagen or collagen-based material.

Statement 73: The composition according to any one of Statements 67-72, wherein the collagen wound care composition comprises from about 20 weight percent to about 50 weight percent oil-based antimicrobial composition.

Statement 74: The composition according to any one of Statements 67-72, wherein the collagen wound care composition comprises from about 20 weight percent to about 40 weight percent oil-based antimicrobial composition.

Statement 75: The composition according to any one of Statements 67-72, wherein the collagen wound care composition comprises from about 15 weight percent to about 35 weight percent oil-based antimicrobial composition.

Statement 76: The composition according to any one of Statements 67-72, wherein the collagen wound care composition comprises from about 15 weight percent to about 25 weight percent oil-based antimicrobial composition.

Statement 77: The composition according to any one of Statements 67-76, wherein the oil-based antimicrobial composition does not separate from the collagen or collagen-based material for at least 6 months.

Statement 78: The composition according to any one of Statements 67-77, wherein the polar solvent comprising one or more antimicrobial agents does not separate from the oil-based carrier for at least 6 months.

Statement 79: The composition according to any one of Statements 67-78, wherein the collagen or collagen-based material is in powdered form.

Statement 80: The composition according to any one of Statements 67-79, wherein the collagen or collagen-based material is characterized by an average particle size of from about 5 microns to about 80 microns.

Statement 81: The composition according to any one of Statements 67-80, wherein the collagen or collagen-based material is prepared with a pH under 4.

Statement 82: The composition according to any one of Statements 67-81, wherein the collagen or collagen-based material comprises a pH under 4.

Statement 83: The composition according to any one of Statements 67-82, wherein the collagen or collagen-based material is bovine collagen or collagen obtained from a bovine.

Statement 84: The composition according to any one of Statements 67-82, wherein the collagen or collagen-based material is Type-1 bovine collagen.

Statement 85: The composition according to any one of Statements 67-82, where in the collagen or collagen-based material comprises a material selected from the group consisting of extracellular matrix materials, micronized extracellular matrix, purified collagen, Type I collagen, Type II collagen, Type III collagen, Type X collagen, collagen fibers, collagen fibrils, micronized collagen, defibrillated collagen, coarse collagen bundles, non-crosslinked collagen, non-mineralized collage, collagen treated to control cross-linking (e.g., via chemical, thermal, photo, or radiation-induced cross-linking), collagen-glycosaminoglycan (GAG) mixtures, and any combination thereof.

Statement 86: The composition according to any one of Statements 67-85, wherein the oil-based based carrier is selected from the group consisting of animal oil, vegetable oil, natural oil, synthetic oil, hydrocarbon oils, silicone oils, and semi-synthetic derivatives thereof, and any combination thereof.

Statement 87: The composition according to any one of Statements 67-86, wherein the oil-based based carrier is selected from the group consisting of is selected from the group consisting of mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, C12-15 alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*Simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combination thereof.

Statement 88: The composition according to any one of Statements 67-87, wherein the oil-based based carrier is coconut oil.

Statement 89: The composition according to any one of Statements 67-87, wherein the oil-based based carrier is petrolatum.

Statement 90: The composition according to any one of Statements 67-89, wherein the oil-based antimicrobial composition comprises greater than about 80% by weight petrolatum.

Statement 91: The composition according to any one of Statements 67-90, wherein the polar solvent is selected from the group consisting of water, ethanol, a mixture of water and ethanol, acetic acid, and any combination thereof.

Statement 92: The composition according to any one of Statements 67-91, wherein the one or more polar antimicrobial agents comprises polyhexamethylene biguanide (PHMB).

Statement 93: The composition according to Statement 92, wherein the oil-based antimicrobial composition comprises from about 0.05% to about 5% by weight PHMB.

Statement 94: The composition according to any one of Statements 67-03, wherein the one or more polar antimicrobial agents comprises a cationic biocide.

Statement 95: The composition according to Statement 94, wherein the cationic biocide is selected from the group consisting of benzalkonium chloride, cetrimide, chlorhexidine, polihexanide biguanide (polihexanide, polyhexamethylene biguanide, polyhexamethylene guanide, poly(iminoimidocarbonyl-iminoimidocarbonyl-iminohexamethylene), poly(hexamethylenebiguanide), polyaminopropyl biguanide), and salts or combinations thereof.

Statement 96: The composition according to any one of Statements 67-95, wherein the polar solvent further comprises a preservative selected from the group consisting of benzalkonium chloride, cetrimide, chlorhexidine, and any combination thereof.

Statement 97: The composition according to any one of Statements 67-96, wherein the oil-based antimicrobial composition comprises from about 0.001% to about 0.15% by weight benzalkonium chloride (BZK).

Statement 98: The composition according to any one of Statements 67-97, wherein the oil-based antimicrobial composition excludes an added emulsifier other than the recited components.

Statement 99: The composition according to any one of the preceding Statements 67-98, wherein the composition is a fluffy collagen matrix or a collagen gel for application to the wound of a subject in need thereof.

Statement 100: The composition according to any one of the preceding Statements 67-99, wherein the collagen wound care composition is prepared by mixing the collagen or collagen-based material with the oil-based antimicrobial composition without heating.

Statement 101: The composition according to any one of the preceding Statements 67-100, wherein the collagen wound care composition is prepared by mixing the collagen or collagen-based material with the oil-based antimicrobial composition at a temperature from about 0 degrees Celsius to about 25 degrees Celsius.

Statement 102: The composition according to any one of the preceding Statements 67-101, wherein the oil-based antimicrobial composition is prepared by a process comprising: a) dissolving the one or more polar antimicrobial agents in a polar solvent to give an antimicrobial agent solution; b) heating the oil-based carrier to a temperature sufficient to cause the oil-based carrier to melt or to a temperature sufficient to provide a oil-based carrier density capable of suspending the polar solvent comprising one or more polar antimicrobial agents, resulting in a melted oil-based carrier; c) heating the antimicrobial agent solution to a temperature higher than the temperature of the melted oil-based carrier to give a heated antimicrobial solution; e) mixing the melted oil-based carrier and the heated antimicrobial solution to give a melted mixture; and f) cooling the melted mixture to give the oil-based antimicrobial composition.

Statement 103: The composition according to Statement 102, wherein the heated antimicrobial solution has a temperature that is about 1° C. to about 5° C. higher than the temperature of the oil-based carrier composition at the time of mixing.

Statement 104: A method of treating or dressing a wound or a post-surgical incisions in a subject, the method comprising applying the composition according to any one of Statements 67-101 to a wound or post-surgical incision in need of dressing or treatment.

Statement 105: The method according to Statement 104, further comprising: contacting the composition according to any one of Statements 67-101 to a wound covering, wherein the wound covering is a selected from the group consisting of a bandage, wrap, gauze, sponge, and film; and applying the wound covering to the wound or post-surgical skin graft in need of treatment.

Statement 106: The method according to Statement 104 or Statement 105, further comprising: packing the wound or post-surgical incision with the composition according to any one of Statements 67-101.

Statement 107: The method according to Statement 106, further comprising: applying a wound covering to the packed wound or post-surgical incision.

What is claimed is:

1. A collagen wound care composition, the composition comprising:
    powdered collagen or powdered collagen-based material; and
    a hydrophobic barrier, wherein the hydrophobic barrier at least partially coats the surface of the powdered collagen or powdered collagen-based material;
    wherein the powdered collagen or powdered collagen-based material comprises from about 45 weight percent to about 85 weight percent of the collagen wound care composition.

2. The composition according to claim 1, wherein the hydrophobic barrier is in the form of a coating at least partially surrounding and adsorbed to the powdered collagen or powdered collagen-based material, the coating effective to reduce the dissolution rate or the rate of absorption of the powdered collagen or powdered collagen-based material when placed in or on a wound in a subject in need thereof.

3. The composition according to claim 2, wherein the hydrophobic barrier prevents the dissolution or absorption of the powdered collagen or powdered collagen-based material when placed on or in a wound or body of a subject for at least seven (7) days.

4. The composition according to claim 3, wherein the wound and/or one or more tissues surrounding the wound is characterized as having a good blood supply.

5. The composition according to claim 1, wherein the hydrophobic barrier comprises one or more oils selected from the group consisting of animal oil, vegetable oil, natural oil, synthetic oil, hydrocarbon oils, silicone oils, and semi-synthetic derivatives thereof, and any combination thereof.

6. The composition according to claim 1, wherein the hydrophobic barrier comprises petrolatum.

7. The composition according to claim 6, wherein the hydrophobic barrier comprises greater than about 80% by weight petrolatum.

8. The composition according to claim 7, wherein the hydrophobic barrier comprises one or more preservatives selected from the group consisting of polyhexamethylene biguanide (PHMB), polyaminopropyl biguanide (PAPB), benzalkonium chloride, cetrimide, chlorhexidine, polihexanide biguanide, polihexanide, polyhexamethylene guanide, poly (iminoimidocarbonyl-iminoimidocarbonyl-iminohexamethylene), and any salt or combination thereof.

9. The composition according to claim 8, wherein the hydrophobic barrier comprises from about 0.05% to about 5% by weight polyhexamethylene biguanide (PHMB) or polyaminopropyl biguanide (PAPB).

10. The composition according to claim 9, wherein the hydrophobic barrier comprises one or more additional preservatives selected from the group consisting of benzalkonium chloride, cetrimide, chlorhexidine, and any salt or combination thereof.

11. The composition according to claim 9, wherein the hydrophobic barrier comprises from about 0.001% to about 0.15% by weight benzalkonium chloride (BZK).

12. The composition according to claim 1, wherein the hydrophobic barrier comprises from about 15 weight percent to about 55 weight percent of the collagen wound care composition.

13. The composition according to claim 1, wherein the hydrophobic barrier comprises a polar solvent, the polar solvent comprising one or more preservatives and suspended in the hydrophobic barrier, wherein the polar solvent is selected from the group consisting of water, ethanol, a mixture of water and ethanol, acetic acid, and any combination thereof.

14. The composition according to claim 13, wherein the hydrophobic barrier excludes an added emulsifier other than the recited components.

15. The composition according to claim 1, wherein the powdered collagen or powdered collagen-based material is characterized by an average particle size of from about 5 microns to about 80 microns.

16. The composition according to claim 1, wherein the collagen wound care composition has a fluffy or unconsolidated consistency suitable for wound packing.

17. A method of treating or dressing a wound or a post-surgical incision in a subject, the method comprising applying the composition according to claim 1 to a wound or post-surgical incision in need of dressing or treatment.

18. The method according to claim 17, further comprising:
    contacting the composition according to claim 1 to a wound covering, wherein the wound covering is a selected from the group consisting of a bandage, wrap, gauze, sponge, and film; and
    applying the wound covering to the wound or post-surgical skin graft in need of treatment.

19. A method of packing a wound in need of dressing, the method comprising:
    packing the wound with the composition according to claim 1; and
    applying a wound covering to the packed wound.

* * * * *